United States Patent
Bose et al.

(10) Patent No.: US 6,666,882 B1
(45) Date of Patent: *Dec. 23, 2003

(54) ENDOVASCULAR THIN FILM DEVICES AND METHODS FOR TREATING AND PREVENTING STROKE

(75) Inventors: Arani Bose, Pelham, NY (US); Peter Kim Nelson, New York, NY (US)

(73) Assignee: New York University, New York, NY (US)

(*) Notice: Subject to any disclaimer, the term of this patent is extended or adjusted under 35 U.S.C. 154(b) by 167 days.

This patent is subject to a terminal disclaimer.

(21) Appl. No.: 09/789,530

(22) Filed: Feb. 22, 2001

Related U.S. Application Data

(63) Continuation of application No. PCT/US99/12444, filed on Jun. 4, 1999.
(60) Provisional application No. 60/087,968, filed on Jun. 4, 1998, and provisional application No. 60/103,575, filed on Oct. 9, 1998.

(51) Int. Cl.[7] .................................................. A61F 2/06
(52) U.S. Cl. ...................... 623/1.15; 623/1.17; 623/1.18
(58) Field of Search ................................ 606/151, 153, 606/154, 155, 156, 198; 623/1.15, 1.18, 1.19, 1.35, 23.7

(56) References Cited

U.S. PATENT DOCUMENTS

| | | |
|---|---|---|
| 4,140,126 A | 2/1979 | Choudhury |
| 4,436,684 A | 3/1984 | White |
| 4,512,338 A | 4/1985 | Balko et al. |
| 4,752,498 A | 6/1988 | Fudim |
| 4,772,530 A | 9/1988 | Gottschalk et al. |
| 4,795,920 A | 1/1989 | Kim |
| 4,842,980 A | 6/1989 | Gottschalk et al. |
| 4,937,159 A | 6/1990 | Gottschalk et al. |

(List continued on next page.)

FOREIGN PATENT DOCUMENTS

| | | |
|---|---|---|
| EP | 0 472 731 A1 | 3/1992 |
| EP | 0 750 886 A1 | 1/1997 |
| EP | 0 752 236 A1 | 1/1997 |
| WO | WO 97/12562 A1 | 4/1997 |
| WO | WO 98/11846 A1 | 3/1998 |
| WO | WO 98/33443 A1 | 8/1998 |
| WO | WO 99/02092 A1 | 1/1999 |

OTHER PUBLICATIONS

Esen et al, "Preparation of monodisperse polymer particles by photopolymerization", *J Colloid Interface Sci* 179:276–280 (1996) (Abstract only).

Hayashi et al, "Elastic properties and strength of a novel small–diameter, compliant polyurethane vascular graft", *J Biomed. Mater. Res.: Applied Biomaterials*, 23(A2):229–224 (1989).

Hill–West et al, "Inhibition of thrombosis and intimal thickening by in situ photopolymerization of thin hydrogel barriers", *Proc Natl Acad Sci USA* 91:5967–5971 (1994).

(List continued on next page.)

*Primary Examiner*—Michael J. Milano
*Assistant Examiner*—P Roberts
(74) *Attorney, Agent, or Firm*—Browdy and Neimark PLLC

(57) ABSTRACT

Devices for excluding aneurysms and treating atherosclerotic disease, for intra-aneurysmal occlusion, and devices for preventing distal emboli. The devices are generally pliable and collapsible thin film devices which can be delivered via a microcatheter into the desired location where they are deployed and undergo either a shape memory phase transformation or in situ polymerization to assume the stable configuration of a permanent endoluminal prosthesis. Prior to being caused to assume their final shape, the devices remain soft, collapsible and pliable to ensure atraumatic delivery through the vascular system. Upon reaching the endoluminal defect in the vessel, the device is extruded from the microcatheter. Devices are also provided for retrieving clots.

14 Claims, 16 Drawing Sheets

U.S. PATENT DOCUMENTS

| | | |
|---|---|---|
| 4,954,415 A | 9/1990 | Davis et al. |
| 4,969,458 A | 11/1990 | Wiktor |
| 4,977,511 A | 12/1990 | Gottschalk et al. |
| 5,061,994 A | 10/1991 | Takahashi |
| 5,089,185 A | 2/1992 | Hirano et al. |
| 5,100,429 A | 3/1992 | Sinofsky et al. |
| 5,122,136 A | 6/1992 | Guglielmi et al. |
| 5,151,520 A | 9/1992 | Gottschalk et al. |
| 5,204,201 A | 4/1993 | Schank et al. |
| 5,211,658 A | 5/1993 | Clouse |
| 5,334,201 A | 8/1994 | Cowan |
| 5,354,295 A | 10/1994 | Guglielmi et al. |
| 5,354,309 A | 10/1994 | Schnepp-Pesch et al. |
| 5,365,996 A | 11/1994 | Crook |
| 5,410,016 A | 4/1995 | Hubbell et al. |
| 5,443,495 A | 8/1995 | Buscemi et al. |
| 5,476,505 A | 12/1995 | Limon |
| 5,518,680 A | 5/1996 | Cima et al. |
| 5,536,274 A | 7/1996 | Neuss |
| 5,540,680 A | 7/1996 | Guglielmi et al. |
| 5,540,701 A | 7/1996 | Sharkey et al. |
| 5,569,245 A | 10/1996 | Guglielmi et al. |
| 5,578,074 A | 11/1996 | Mirigian |
| 5,607,467 A | 3/1997 | Froix |
| 5,609,629 A | 3/1997 | Fearnot et al. |
| 5,626,863 A | 5/1997 | Hubbell et al. |
| 5,662,712 A | 9/1997 | Pathak et al. |
| 5,665,063 A | 9/1997 | Roth et al. |
| 5,683,411 A | 11/1997 | Kavteladze et al. |
| 5,741,323 A | 4/1998 | Pathak et al. |
| 5,800,517 A | 9/1998 | Anderson et al. |
| 5,800,525 A | 9/1998 | Bachinski et al. |
| 5,814,064 A | 9/1998 | Daniel et al. |
| 5,846,247 A | 12/1998 | Unsworth et al. |
| 5,849,035 A | 12/1998 | Pathak et al. |
| 5,876,434 A | 3/1999 | Flomenblit et al. |
| 5,882,444 A | 3/1999 | Flomenblit et al. |
| 6,004,261 A | 12/1999 | Sinofsky et al. |
| 6,007,544 A * | 12/1999 | Kim ........................ 606/108 |
| 6,302,906 B1 * | 10/2001 | Goicoechea et al. ....... 623/1.11 |
| 6,315,794 B1 * | 11/2001 | Richter ...................... 623/1.34 |
| 6,409,755 B1 * | 6/2002 | Vrba ........................... 623/1.2 |
| 6,428,567 B2 * | 8/2002 | Wilson et al. ............. 623/1.11 |
| 6,436,104 B2 * | 8/2002 | Hojeibane ................... 606/108 |

OTHER PUBLICATIONS

Johnson et al, "Fabrication of Silicon–Based Shape Memory Alloy Micro–Actuators", *Mat. Res. Soc. Symp. Proc.* vol. 276, pp. 151–160 (1992).

Slepian, "Polymeric Endoluminal Paving", *Cardiol Clin* 12(4):715–737 (1994).

Tanguay et al, "Current status of biodegradable stents", *Cardio Clin* 12(4):699–713 (1994).

Torres–Filho et al, "Mechanical Properties of Acrylate Networks Formed by Visible Laser–Induced Polymerization. I. Dependence on Photopolymerization Parameters", *J App Polymer Sci* 51:931–937 (1994).

Microvena Corporation kit label for Amplatz "Goose neck" Snare and catalog entry concerning the "Amplatz 'Goose neck' Snares and Microsnares".

* cited by examiner

501

602
601

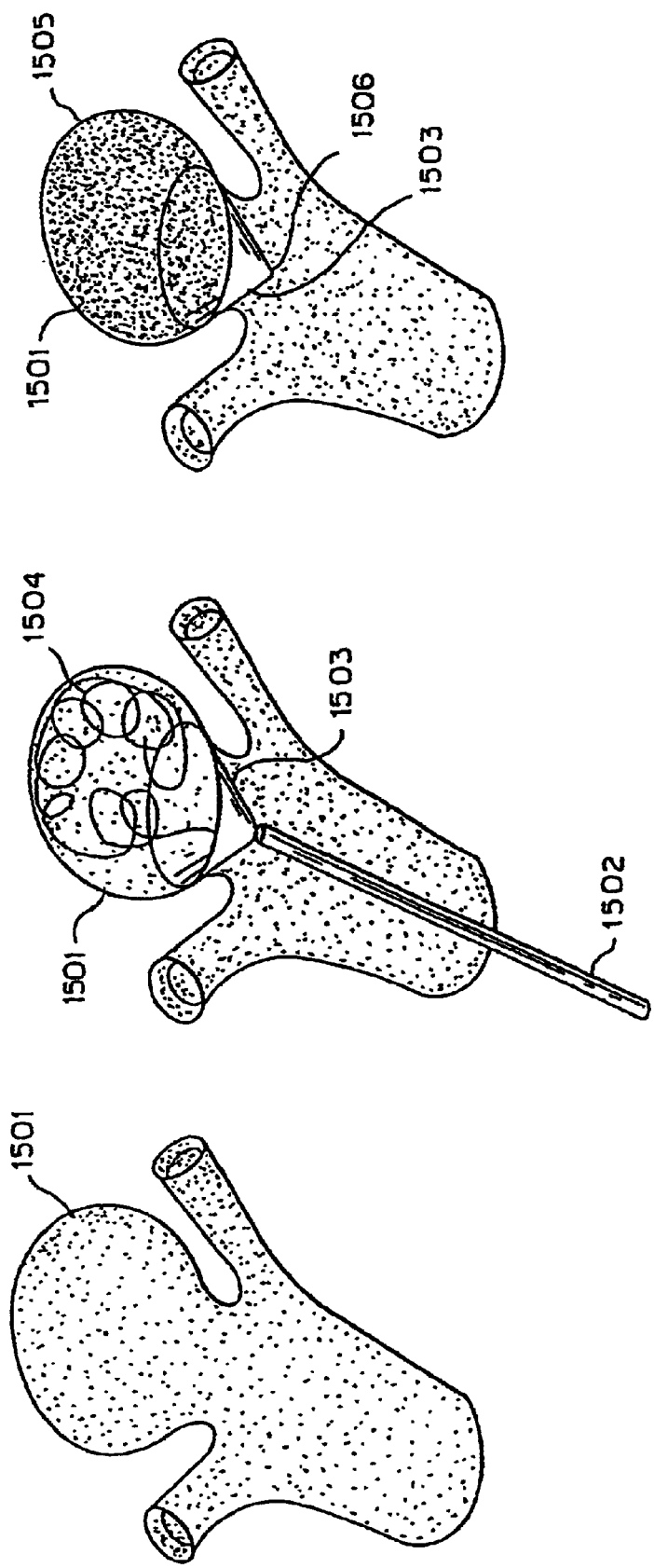

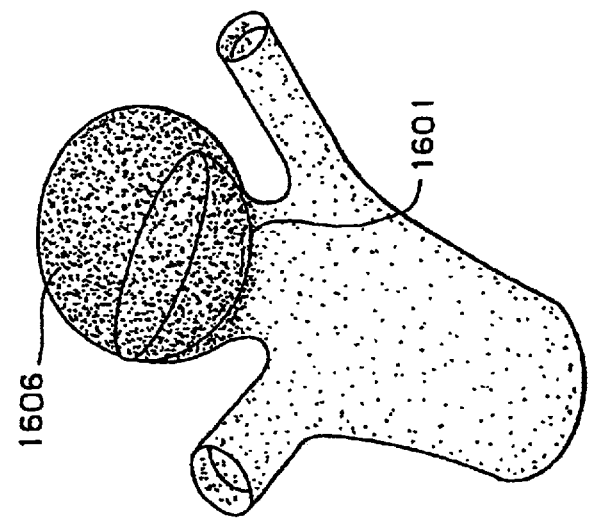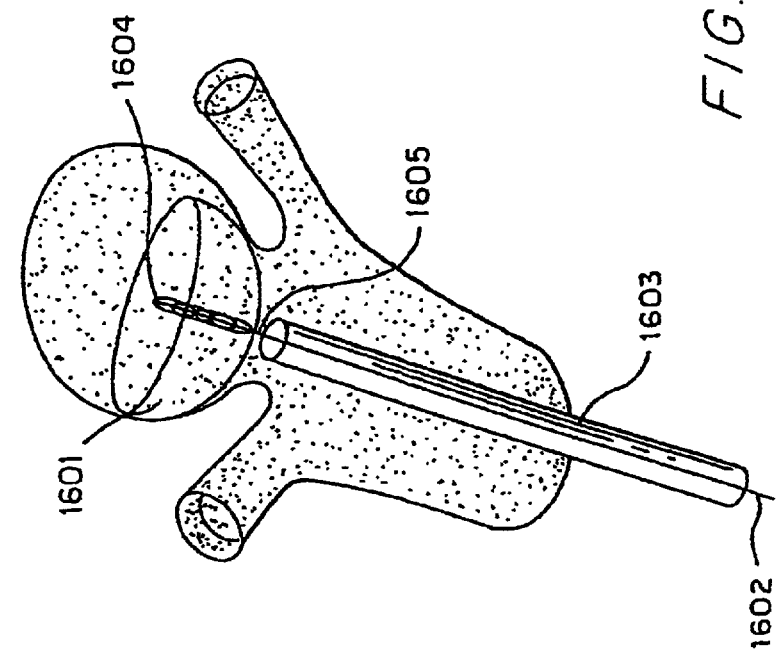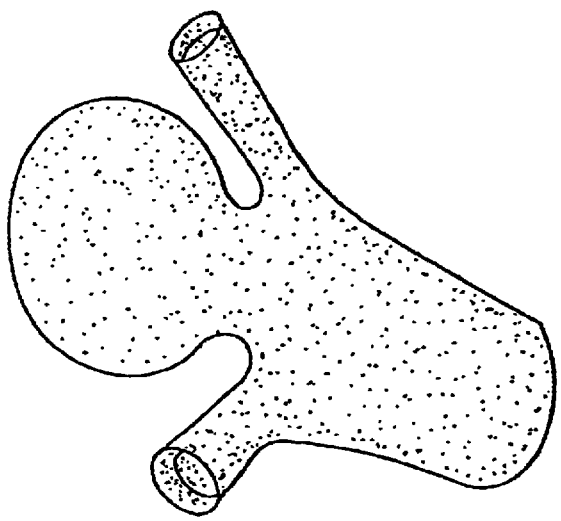
FIG. 16A
FIG. 16B
FIG. 16C
FIG. 16D

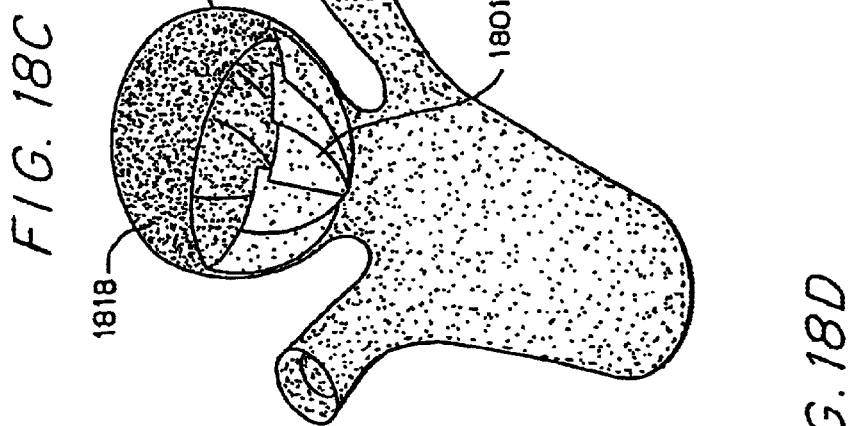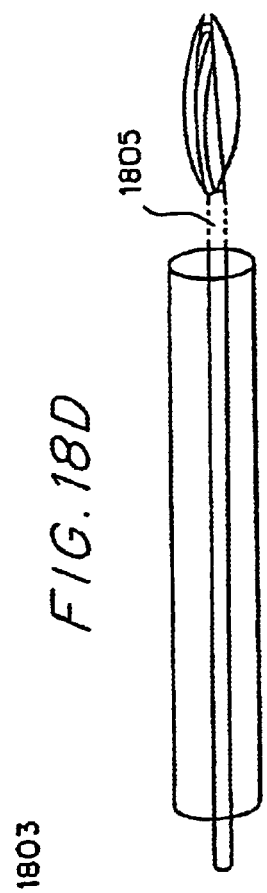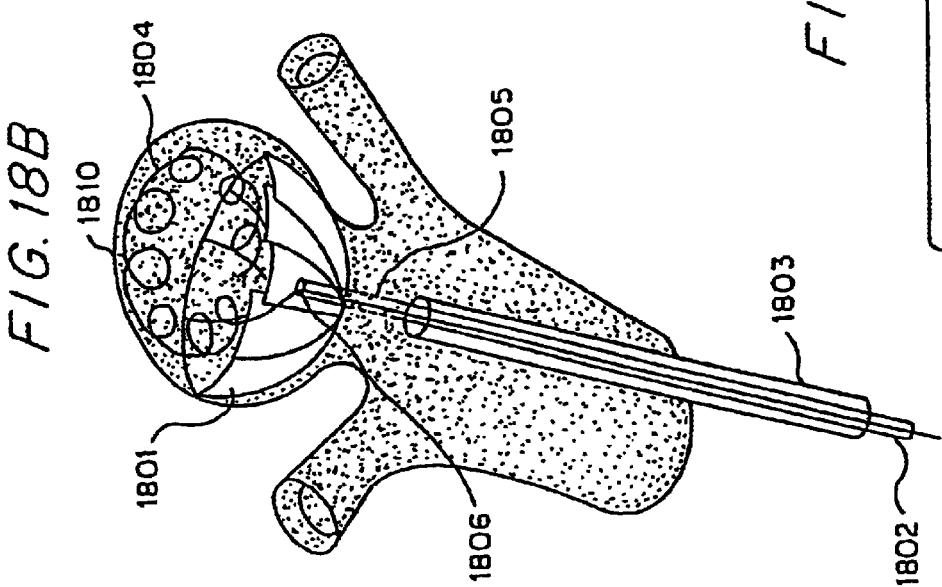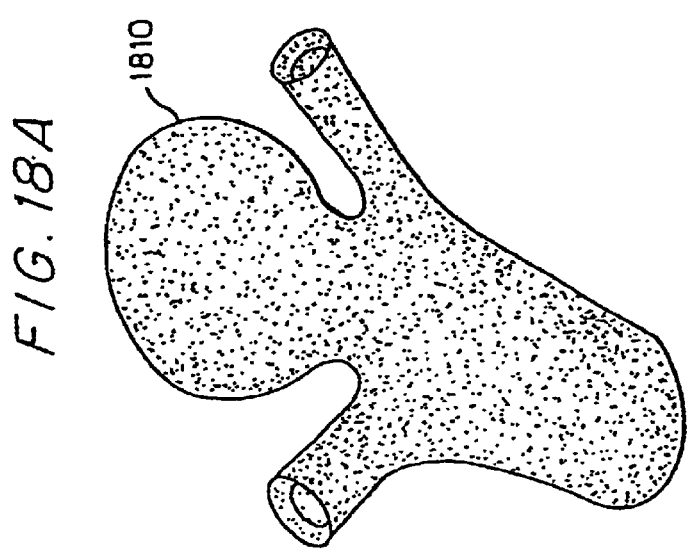

ENDOVASCULAR THIN FILM DEVICES AND METHODS FOR TREATING AND PREVENTING STROKE

This is a continuation of parent application Ser. No. PCT/US99/12444, filed Jun. 4, 1999.

CROSS-REFERENCE TO RELATED APPLICATIONS

The present application is related to U.S. provisional applications No. 60/087,968, filed Jun. 4, 1998, and Ser. No. 60/103,575, filed Oct. 9, 1998, the entire contents of each of which are hereby incorporated herein by reference.

FIELD OF INVENTION

The present invention is directed to endovascular thin film devices which can be used for treating and preventing stroke, including ischemic stroke caused by a blood clot in a blood vessel in the brain or hemorrhaging stroke caused by aneurysmal subarachnoid hemorrhage.

BACKGROUND OF INVENTION

Cerebrovascular disease is the third leading cause of death in the USA and the leading cause of disability. Strokes affect 500,000 Americans every year. This results in 150,000 stroke-related fatalities per annum, and over 3,000,000 stroke survivors (Wieber et al, *Stroke* 23:10, 1992). The cost to the community, including health care expenses and lost productivity, has been estimated at over $30 billion per annum. Neurovascular disorders resulting in thromboembolic occlusion of intracranial arteries, resulting in ischemic stroke, and rupture of intracranial aneurysms, resulting in hemorrhagic stroke, are major contributors to stroke-related morbidity and mortality world wide. In contrast to cardiovascular disorders, endovascular treatment strategies for neurovascular disorders have been historically limited by issues of safe access to the cerebral vasculature. Over the past decade advances in digital subtraction angiographic techniques and improvements in microcatheter and microguidewire technology have significantly broadened the scope of minimally invasive neuroendovascular therapy. Today, there is an urgent need for developing medical devices specially designed for deployment via catheter-based techniques for percutaneous endovascular treatment of various devastating neurovascular disorders.

Recent clinical data suggest that patients with acute occlusion of intracranial arteries benefit from rapid removal of the intra-arterial clot and experience an improved outcome. Until now, intracranial clot removal has been primarily accomplished by anticoagulation and thrombolysis. There are several disadvantages to this method of clot removal. First, the clot composition in many patients makes it not feasible to use urokinase or TPA for thrombolysis. Second, if clot lysis is successful, the problem of reperfusion hemorrhage within the distal vascular bed is dramatically magnified due to the patient's anticoagulated condition at the time of reperfusion due to prior administration of thrombolytics and heparin. Third, removal of clot by lysis is much more likely to result in distal embolization of small blood clots in a vascular territory that is at the end arteriorlar level and is beyond the help of collateral circulation from adjacent vessels. Due to these shortcomings, an ideal clot removal system would involve mechanical removal of the blood clot from the intracranial vessel without disruption of the patient's coagulation cascade.

In managing peripheral and coronary atherosclerotic vascular diseases, percutaneous transluminal angioplasty (PTA), usually in combination with percutaneous stent placement, is an alternative to surgical revascularization (Mayberg et al, *JAMA*, 266:3289–3294, 1991; Moiore et al, *Stroke* 26:188–201, 1995). There is a growing body of experience with these techniques in the carotid and vertebrobasilar arteries (O'Keefe et al, *JACC* 16:1097–1102, 1990; Becker et al, *Radiology* 170:921–940, 1989). Various investigators have stented over 100 arteries with technical success in 95 to 99% of vessels. In addition, the morbidity and mortality rates are comparable to those of CEA (stroke rates of 0–8%, incidence of death 0–0.9%, and restenosis rates of 1–8%). Similar efficacy and safety is observed in angioplasty and stenting of other supra-aortic vessels. Together these data suggest that carotid angioplasty and stenting (CAS) is safe, feasible, and a viable alternative to CEA in the treatment of patients with carotid atherosclerotic disease.

There are two major potential limitations of PTA in managing arterial stenosis: restenosis and distal embolism. Although there is limited long-term follow-up after supra-aortic PTAs, several studies suggest that the restenosis rate is less than 10 at 12 months. This is similar to the results of angioplasty in other vessels where the restenosis rate is related to the size of the vessel and type of lesion. Large vessels such as the iliac and proximal femoral arteries have restenosis rates of 20–25% at three years, while smaller vessels (popliteal and coronary arteries) have restenosis rates of 35–45% (Kachel et al, *Neuroradiology* 33:191–194, 1991; Criado et al, *American Journal of Surgery* 174:111–114, 1997). Following CEA restenosis may occur in up to 36% of vessels after a two to ten-year follow up. Placing a stent across the vascular segment which has been dilated by PTA reduces the rate of restenosis.

During CEA, transcranial Doppler (TCD) monitoring studies have suggested that emboli may be responsible for half of the cerebrovascular complications of this procedure (Moore et al, *Stroke* 26:188–201, 1995). A small study has compared TCD of the middle cerebral artery in patients undergoing CEA or PTA (Sundt et al, *Mayo Clin. Proc.* 50:301–306, 1975). CEA was associated with longer occlusion times and greater reductions in ipsilateral MCA velocity. In contrast thereto, PTA was associated with more micro-embolic signals.

There is an urgent need to develop specially designed medical devices to address the issues of post-angioplasty restenosis and to provide distal protection from thromboemboli during PTA. Stents and stent grafts whose size and compliance characteristics are uniquely suited for the carotid vasculature and the vertebro-basilar system both intra- and extracranially are still not commercially available and sorely needed. In addition, distal protection devices that allow continuous distal cerebral perfusion while preventing distal emboli would dramatically improve the safety and feasibility of luminal reconstruction in the cerebral vasculature.

Aneurysmal subarachnoid hemorrhage is a major cause of death and disability in a relatively young patient population. There is an annual incidence of aneurysmal subarachnoid hemorrhage of approximately 10–12 per 100,000 population in most western countries. In the United States nearly 40,000 individuals are hospitalized with aneurysms yearly (Wieber et al, 1992). The natural history of the disease is such that over 30% of patients will die within 24 hours of the bleed, and another 25–30% will succumb in the next four weeks without some form of intervention. As recently as 1993 the only therapeutic option for these patients was surgical management. In the United States, 55–65% of patients suffering aneurysmal subarachnoid hemorrhage do not receive surgical treatment due to their poor medical condition, advanced age, or other factors. This patient population is, instead, relegated to a conservative medical management regimen. The outcome for such non-surgical patients is dismal, with approximately 60% mortality and 25–40% morbidity reported within six months of the original bleed (Weir, *Aneurysms Affecting the Nervous System*, Chapter II, pp. 19–54, 1987).

Endovascular techniques for the treatment of intracranial aneurysms have been evolving over the past ten or fifteen years. Historically, the endovascular treatment of intracranial aneurysms has been fraught with significant intraoperative morbidity and mortality and poor clinical outcome. Endovascular occlusion has been attempted with a variety of materials from balloons to iron microspheres. The Guglielmi detachable coil, which has been in use in Europe since 1992 and in North America since 1991, provided a major technical advance. Endovascular treatment of intracranial aneurysms has been performed in approximately 4,000 patients worldwide with the Guglielmi detachable coil and has significantly improved the treatment modality by providing a technically safer and more reliable occlusion system.

Data from medical centers with significant endovascular experience suggest complication rates of aneurysm treatment following subarachnoid hemorrhage to be in the range of 1.5–5% mortality and 3–5% morbidity (Byrne et al, *J. Neurology, Neurosurgery and Psychiatry*, 59(6):616–620, 1995). Post treatment rebleeding rates are less than 1% of treated patients. The treatment modality of the Guglielmi detachable coil involves endovascular microcatheterization of the aneurysm lumen using a coaxial catheter system from a common femoral artery approach. Electrolytically detachable platinum coils are then extruded through the microcatheter and deposited within the aneurysm lumen, thereby filling the aneurysm and excluding the aneurysm lumen from the intracranial circulation and protecting the aneurysm from rupture. This methodology can be effective in the treatment of saccular aneurysms and aneurysms in which the neck to dome ratio is small.

Since its introduction in 1991, the Guglielmi detachable coil has provided a safe, effective, and reproducible endovascular platform for accessing aneurysms throughout the intracranial circulation. However, limitations of the technology have become apparent related to incomplete occlusion of the aneurysm lumen or coil compaction, which results in recanalization of the aneurysm. These limitations are most apparent with particular types of aneurysmal configurations. Wide neck aneurysms or aneurysms that have a small neck but an equally small dome are often not amenable to definitive surgical repair and are difficult or impossible to treat using the Guglielmi detachable coil. In addition, non-saccular intracranial aneurysms, such as fusiform aneurysms and dissecting aneurysms, as well as pseudo aneurysms of intracranial and extracranial vessels, are not adequately treated by surgery or by current endovascular techniques. Examples of this technique can be found in U.S. Pat. Nos. 5,122,136, 5,354,295, and 5,569,680, as well as European Patent No. 750,886.

Stents have historically been used for revascularization to limit abrupt reclosure and restenosis of blood vessels. However, in the case of stents for revascularization, permanent implants have the disadvantage of treating a time-limited disease process, namely post-angioplasty restenosis, which has significant biochemical and cellular mechanisms contributing to its pathogenesis. Slepian (*Cardiology Clinics* 12(4):715–737, 1994) discloses polymeric endoluminal paving in which biocompatible polymers are applied to the endoluminal surface of an organ and custom-contoured in situ via a catheter to yield a layer or film of polymer in contact with the underlying tissue surface. These tubes or sheets of biodegradable polymers are transported intravascularly via a catheter and positioned at the lesion site and locally remodeled via intraluminal thermoforming of the base line material. Alternatively, fluids are applied to the tissue surface to act as a short-term, thin, chemical interface layer. Another method is to use a polymer film containing interspersed photo-absorbant dye. This method has been used in dissected canine carotid arteries in vitro. However, Slepian recognized that a permanent stent has many disadvantages in preventing restenosis of a blood vessel, and, thus, only biodegradable polymers are used. Slepian used thin tubes or sheets of biodegradable polymers which were transported intravascularly via a catheter and positioned at the lesion site. The polymer is locally remolded via intraluminal thermoforming of the baseline material.

Stereolithography, which is the subject of U.S. Pat. No. 4,575,330, to Hull, is used to form solid shaped objects using computer-generated surface model data to direct an ultraviolet or other laser beam to polymerize a photosensitive mixture of initiators and monomers, such as acrylate monomers. Photopolymerization of multiacrylate monomers up to a thickness of 50 microns has been demonstrated using ultraviolet light radiation in the wave length of 360 nm (Snesen et al, *J. Colloid Interface Sci.* 179:276–280, 1996). Recently, more powerful and reliable visible lasers, such as $Ar^+$, have been used as the radiation source for the photopolymerization process (Kumar et al, *Macromolecules* 24:4322, 1991). In addition, mechanical properties of acrylate networks, such as tensile strength, elasticity, and stress response, can be altered by manipulating various photopolymerization parameters (Torres-Filho et al, *J. Applied Polymer Science* 51:931–937, 1994).

Polymer application to endoluminal surfaces has been pursued for some time in the cardiovascular system. Polymer stents have been investigated as potential alternatives to metal stents in the coronary circulation (van Beusekom et al, *Circulation* AB6(supI):I-731, 1992). In addition, chemical processes allowing a polymer to mold and adapt to the underlying tissue topography while generating a smooth balloon molded endoluminal surface have been investigated (Slepian, 1994). Thin hydrogel barriers have been formed on the inner surface of explanted carotid arteries in a rat and rabbit model by in situ photopolymerization in vitro. The illumination conditions in this laboratory model could be varied to control the thickness of the barrier from 10 microns to more than 50 microns (Hill-West et al, *Proc. Nat. Acad. Sci. USA* 91:5967–5971, 1994).

The last several years have seen significant technological advancement in the application of shape memory alloys in medical devices. Materials with shape memory undergo a phase transformation in their crystal structure under certain specific conditions. This phase transformation, which is inherent within the material, is the basis for the material's unique properties of shape memory and superelasticity. Examples of such applications are found in Kim, U.S. Pat. No. 5,797,920 and Anderson et al, 5,800,517.

A variety of vascular stents have been proposed. However, none of these has been entirely successful in treating or prevention stroke.

Cowan, in U.S. Pat. No. 5,334,201, describes a permanent vascular reinforcing stent made of a cross-linkable material. A cross-linkable substance is completely encapsulated within a biologically compatible film. Once the stent is in place, a fiber optic means is used to transmit light from a source to a light-emitting tip which is passed inside the catheter to cause the cross-linkable material to cross-link. In this case, the stent is a radially-expansible tubular body portion which is composed of a cross-linkable substance. The stent is not sufficiently pliable to negotiate the tortuous curves of the carotid artery within the skull base. Moreover, the cross-linking technique used by Cowan requires that the balloon be expanded during the entire cross-linking process, thus inhibiting blood flow to the brain. This technique cannot be used in the intracranial circulation, because blood flow to the brain cannot be occluded for a period of time sufficient to cure the polymers used.

Hubbell et al, in U.S. Pat. Nos. 5,410,016 and 5,626,863, disclose photopolymerizable biodegradable hydrogels which can be used to hold vessels or tubes in a particular position for a controlled period of time. Of course, since the hydrogels only remain in the body for a controlled period of time, these hydrogels would not be useful in permanently closing off an aneurysm.

Fearnot et al, in U.S. Pat. No. 5,609,629, disclose an implantable medical device that provides a controlled release of an agent, drug, or bioactive material into the vascular or other system in which a stent or other device is positioned. The polymer can be applied as a coating to a stent, which is preferably composed of a biocompatible material, such as a biocompatible metal.

Buscemi et al, in U.S. Pat. No. 5,443,495, disclose a balloon/stent device for enlarging in situ to fit against a vessel wall, after which the stent is hardened in place. If the material in the stent is activated by light energy, the center shaft of a catheter which introduces the stent to the appropriate location contains an optical fiber.

Choudhury, in U.S. Pat. No. 4,140,126, discloses a method for repairing an aneurysm using a prosthetic graft. The graft comprises an elongated tube which is moveable into a collapsed formation wherein a plurality of folds which extend longitudinally for the length of the tube are interspersed with a plurality of radially-spaced anchoring pins. The tube is preferably collapsed around a carrier line, such as a modified catheter tube, for introduction to the site.

Regan, U.S. Pat. No. 4,795,458, discloses a stent for use after balloon angioplasty made of any nitinol alloy. The stent is in the shape of a helical coil. The stents are treated to make them non-thrombogenic.

Kelly et al, U.S. Pat. No. 5,769,871, disclose an embolectomy catheter for removing an embolus within a vessel, and also review prior devices for removing emboli. Kelly et al do not us a balloon for retrieving material within a blood vessel but use a hollow shaft with a flexible hollow polymeric tip disposed distally off a hingedly flexible annular compartment. The device is pulled through the vessel via a pull on the handle to collect any embolus within.

Dayton, U.S. Pat. No. 5,449,382, discloses a stent which includes a plurality of holes patterned with a desired size, shape, and number to provide a desired bending modulus. This stent is then coated with a polymer or is formed from a polymer which contains a bioactive substance. In this case the holes provide the desired bending.

Winston, in U.S. Pat. Re. Nos. 35,988 and 5,306,294, discloses a stent in the form of a flexible metal sheet which is closely wound around a spool in a spiral roll. This stent is preferably constructed of a stainless steel foil of about 0.0005 inch thickness. The sheet produces an inherent spring force which expands the sheet from the contracted position in which it is inserted into a vessel.

There are a number of patents which disclose systems for capturing emboli. Daniel et al, 5,814,064, disclose an emboli-capturing system including an expandable member coupled to a mesh which can be formed in the shape of a cone to capture emboli.

Bourne et al, U.S. Pat. No. 5,649,950, disclose a system for retrieval of a prosthetic occluder. The occluder is formed of a mesh substance and is delivered in a collapsed state.

Ginsburg, U.S. Pat. No. 4,873,978, discloses a vascular catheter including a strainer device at its distal end to capture emboli. The strainer device is in open position when placed in a blood vessel to capture emboli, and in a closed configuration where it is able to retain any captured emboli within its confines.

Kavteladze et al, U.S. Pat. No. 5,683,411, disclose a stent comprising a self-expanding body shaped into the form of a body of revolution, part of which is formed by wire members forming cells of a generally polygonal shape. The body of revolution has a diameter increasing continuously in an axial direction of the body from one end forming an apex towards the opposite end forming a base. This body an be used as an intravenous filter for capture of thrombi or in combination with a blood impermeable membrane as an occlusion device for closing a vessel lumen.

The patents to Lefebvre, U.S. Pat. No. 4,990,156; Elsberry, WO 96/33756; Simon, U.S. Pat. No. 4,425,908; Miller et al, U.S. Pat. No. 5,549,626; Summers et al, U.S. Pat. No. 5,695,519; and Dibie et al, U.S. Pat. No. 5,413,586, all disclose other types of devices for capturing emboli.

Balko et al, U.S. Pat. No. 4,512,338, disclose a stent made of nitinol wire in the shape of a longitudinally oriented coil of adjacent wire loops which is used for restoring patency to an aneurysm. Wiktor, U.S. Pat. No. 4,969,458, discloses a vascular stent made of low memory metal which provides radial support from within a blood vessel. This stent is such that the wire is coiled having a limited number of turns wound in one direction, then reversed and wound in the opposite direction with the same number of turns, then reversed again, etc. This configuration allows for radial expansion of the stent when controlled pressure, such as applied by an inflated balloon, is applied from the inside of the stent.

Mirigian, U.S. Pat. No. 5,578,074; Sharkey et al, U.S. Pat. No. 5,540,701; Neuss, U.S. Pat. No. 5,536,274; Limon, U.S. Pat. No. 5,476,505; Schnepp-Pesch et al, U.S. Pat. No. 354,309; Bosley, Jr. et al, U.S. Pat. No. 5,514,176; Froix, U.S. Pat. No. 5,607,467; and Flomenblit et al, U.S. Pat. No. 5,876,343, and U.S. Pat. No. 5,882,444, all show other types of coiled stents.

Unsworth et al, U.S. Pat. No. 5:846,247, and McNamara et al, U.S. Pat. No. 147,370, disclose tubes made from shape memory alloys for use in body tubes.

Cima et al, in U.S. Pat. No. 5,518,680, disclose the use of stereolithography for making tissue regeneration matrices. While the technique can be used for soft tissues, such as blood vessels, there is no indication that this technique can be used in vivo to repair aneurysms.

It would be desirable to develop a medical device platform to improve endovascular treatment options for ischemic and hemorrhagic stroke. Of significant importance is the ability to safely and permanently exclude areas of aneurysmal weakness in the neurovascular circulation, thereby preventing initial or recurrent aneurysmal subarachnoid hemorrhage, as well as ischemic stroke. In addition, low-profile, thin film stents and stent grafts will enable endoluminal reconstruction on the neurovascular circulation and other applications where the internal diameter is small and the route is tortuous. It is also important to be able effectively to retrieve blood clots from the intracranial circulation without altering the body's coagulation cascade.

SUMMARY OF THE INVENTION

It is an object of the present invention to overcome the aforementioned deficiencies in the prior art.

It is another object of the present invention to provide thin film devices for use anywhere in the body, including the vasculature.

It is another object of the present invention to provide methods and apparatus for treating and preventing ischemic and hemorrhagic stroke.

It is another object of the present invention to provide a platform for endovascular treatment for aneurysms in the intracranial circulation.

It is another object of the present invention to provide a method for safely and permanently excluding areas of aneurysmal weakness in the neurovascular circulation, thereby preventing initial or recurrent aneurysmal subarachnoid hemorrhage.

It is still another object of the present invention to provide endovascular thin film devices made of sputtered shape memory alloy thin film.

It is another object of the present invention to provide endovascular thin film devices made of photo-activated monomers encased in a thin biocompatible membrane.

It is a further object of the present invention to provide thin film devices to restore patency to any vessel in the body.

According to the present invention, several types of thin film devices are provided which can be used for treating deficiencies in the vasculature, trachea, esophagus, etc., particularly for treating or preventing ischemic or hemorrhagic stroke:

1. A clot retriever for the acute treatment of ischemic stroke.

2. A platform of devices for intra-cranial stenting for excluding aneurysms and treating atherosclerotic disease. These devices comprise several embodiments broadly referred to as an endoluminal sleeve. The endoluminal sleeve is best suited for treating sidewall aneurysms, fusiform aneurysms, and dissecting aneurysms. The sleeve is located outside of the aneurysmal dilatation within the parent vessel and excludes the aneurysm from the circulation while reconstructing the lumen of the parent vessel. The sleeve can also be used in other areas of the body, e.g., the trachea, colon, and the like.

In one embodiment a conformal sleeve is placed outside the aneurysm to exclude the aneurysm from the circulation. The sleeve is placed in the parent vessel. The sleeve can be optionally fenestrated. The sleeve can be segmented to facilitate its placement around a bend in the vessel. The attachments between segments can be in a linear or a helical configuration. The thin film sleeve in one embodiment can also be bifurcated in order to treat saccular bifurcation aneurysms.

In another embodiment of the endoluminal sleeve the thin film material is in the configuration of a rolled thin film sheet with optional interlocking tabs, and with optional fenestrations. The optional fenestrations can be configured to provide near complete coverage of the vessel, as in a covered stent, or for minimal and selective coverage of the vessel wall, as in an endovascular patch, to cover only the aneurysm neck. This design allows for a favorable expansion ratio from a tightly rolled sleeve with multiple overlapping layers for introduction into a blood vessel, to a less rolled configuration with fewer layers of overlap in the deployed state within the blood vessel providing for an endoluminal reconstruction of the blood vessel wall. The sleeve can also be in the form of overlapping rings, which are optionally fenestrated.

3. A platform of endovascular thin film devices for intra-aneurysmal occlusion, provided in several embodiments.

These devices are best suited for treating saccular bifurcation aneurysms, and include a thin film funnel and a thin film hemisphere in the shape of an inverted umbrella. The thin film hemisphere may be made of a single membrane or a series of overlapping membranes.

In another embodiment, the thin film aneurysm occlusion device is in the shape of a sphere or ellipse to be placed within the aneurysm. The proximal half of the sphere, which covers the aneurysm neck, can be a solid membrane in order to occlude the neck of the aneurysm. However, the distal half of the sphere is a largely fenestrated membrane through which a variety of aneurysm occlusion devices can pass, such as polymers, coils, hydrogels, etc. In this manner the coils or hydrogel mass can pass through large fenestrations in the intra-aneurysmal sphere and anchor the thin film intra-aneurysmal device within the aneurysm lumen.

All of the endovascular thin film devices of the present invention are deployed inside the aneurysm, leaving the parent vessel unaffected. All of these endovascular thin film devices may be deployed via a hollow delivery guide assembly or a solid delivery guide assembly. In the embodiment covering the hollow delivery guide assembly, the hollow delivery guidewire or guide catheter may have a one-way valve at its distal tip. This allows introduction of a volume-filling device, such as a polymer or hydrogel or coils, but would trap these coils of hydrogel or polymer within the aneurysm due to the one-way nature of the valve. All of the aneurysm treatment devices, both the extra-aneurysmal devices, such as the sleeve, or the intra-aneurysmal devices, such as the funnel, hemispheres, or spheres, are detachable devices serving as endoluminal implants. In an additional embodiment, they may also serve as non-implantive devices for aneurysm neck remodeling during endovascular treatment.

4. Also provided are endovascular thin film devices for preventing distal emboli while maintaining antegrate flow within the vessel.

Intracranial Stent Devices

In one embodiment of the present invention, an endoluminal conformal sleeve is provided which is a pliable and collapsible device that is delivered via a microcatheter into the intracranial circulation where it is deployed and undergoes either a shape memory phase transformation or in vivo polymerization to assume the stable configuration of a permanent endoluminal prosthesis. In the inactive state the sleeve remains soft, collapsible, and pliable to ensure its atraumatic delivery through the tortuous curves of the cavernous carotid artery. Upon reaching the endoluminal defect at the site of the aneurysm, the endoluminal conformal sleeve is extruded from the microcatheter. A thin biocompatible membrane with shape memory characteristics is deployed within the vascular lumen where it unfolds to assume a low-profile cylindrical shape of predetermined diameter and length. Alternatively, a thin biocompatible membrane envelope containing a macromolecular precursor is deployed within the vascular lumen where it unfolds to assume a low-profile cylindrical shape of predetermined diameter and length. The soft and pliable sleeve may be segmented to follow the curve of the vessel and conform to its luminal contour. The dimensions are selected so as to provide accurate coverage of the entire base of a saccular aneurysm or the entire length of a fusiform or dissecting aneurysm. Upon deployment, selective angiography can be performed to demonstrate adequate exclusion of the aneurysm from the intracranial circulation. If the position of the endoluminal sleeve is deemed to be inadequate, the collapsible prosthesis can be retracted back into the microcatheter delivery system and removed. After accurate positioning, the conformal sleeve is activated and/or detached.

The endoluminal conformal sleeve of the present invention is formed in situ by constructing the endoluminal conformal device from a material that is able to undergo shape deformation repeatably between two specific predetermined shapes as a function of an applied stimulus. This type of behavior in a material is referred to as dual shape memory effect. Alternatively, the endoluminal conformal sleeve of the present invention can be formed in situ via polymerization of a suitable polymer-forming network or precursor. Polymerization is initiated by suitable polymerization initiators in any combination, such as by heat, light, catalyst, electric field, magnetic field, sonic energy, or any other type of polymerization initiator that can be used to polymerize the precursor in situ.

Intra-aneurysmal Occlusion Devices

In an other embodiment, the endovascular thin film device is in the form of an endoluminal conformal funnel. The funnel is composed of a collapsible thin film biocompatible membrane with shape memory characteristics which, upon extrusion from a microcatheter, unfolds within the aneurysmal lumen to occlude the aneurysm orifice. The configuration of the funnel is such that its distal diameter is larger than the aneurysm neck and tapers to a smaller proximal orifice with an optional one-way valve through which a packing material may be introduced into the aneurysm fundus in the deployed state. The packing material may include a polymerizing substance, hydrogel, or metallic coil device. These devices can be mechanically deployed within the aneurysm or can be remotely triggered via the introducing guidewire assembly to undergo a phase transformation, thereby filing the aneurysm volume and serving to anchor the funnel at the aneurysm base by exerting radial tension on the funnel membrane, preventing it from migrating from or within the aneurysm.

In another embodiment, the endovascular thin film device may be an umbrella shaped dome or hemisphere composed of a single membrane mounted on a solid introducing guidewire assembly. In yet another embodiment, the endovascular thin film device may be composed of a sphere such that the proximal half of the sphere is a single membrane non-fenestrated dome, while the distal half of the sphere is a richly fenestrated dome. The fenestrations within the distal hemisphere allow the aneurysm volume-filling material to pass freely through the aneurysm occluding sphere and thereby anchor the endovascular thin film device at the aneurysm neck and base by exerting radial tension on the spherical or elliptical endovascular thin film device, holding it in place against the aneurysm dome. The aneurysm volume-filling material may be a shape memory material that is incorporated within the concavity of the dome of the hemispherical device or the spherical or elliptical device. This shape memory material can undergo a triggered phase transformation and expand to fill the aneurysm volume, thereby anchoring the funnel or sphere at the base of the aneurysm by exerting radial tension on the thin film device and preventing it from migrating from or within the aneurysm.

In another embodiment, the endovascular thin film device may be constructed of separate overlapping component membranes which unfold after being extruded from the lumen of the introducing microcatheter and assume the shape of a blossoming flower bud. If a shape memory material that can undergo a triggered phase transformation and expand to fill the aneurysm volume is incorporated within the concavity of the flower bud, analogous to a stamen, the device can be mounted on a solid introducing guidewire assembly. This device undergoes a triggered phase transformation to expand to fill the aneurysm volume, thereby anchoring the funnel at the aneurysm base by exerting radial tension on the funnel membrane, thus preventing it from migrating from or within the aneurysm.

Alternatively, the device may be mounted on a hollow guidewire or guide catheter assembly such that, after deployment of the device, the internal volume of the aneurysm may be accessed through the hollow guidewire and filled with a packing material. Access may be restricted via a one-way valve. This allows filling of the aneurysm volume but contains the volume-filling material within the aneurysm due to the one-way nature of the valve. A variety of packing materials may be used, such as shape memory material, polymerizing material, hydrogel, coils, or other materials or devices, to fill the aneurysm volume and thereby anchor the funnel at the aneurysm base by exerting radial tension on the funnel membrane and preventing it from migrating from or within the aneurysm.

The thin film membranes that compose the device are folded on themselves via stress-induced deformation according to the superelastic properties of the shape memory materials. The device is deployed by extruding ,it from the catheter, thereby removing the stress and allowing it to revert to its undeformed configuration. Alternatively, the dual shape memory properties of the material may be used and a triggering stimulus provided to induce a phase transformation. After deployment of the device and prior to filing the internal volume of the aneurysm, the device can be retracted into the catheter and removed from the patient if the size and shape characteristics of the device are unsuitable for the local angio-architecture.

In the case in which there is a circumferential endoluminal lining caused by placing the sleeve which may interfere with perfusion of adjacent perforating arteries or vascular branches, the endoluminal sleeve is fenestrated. The fenestrations permit blood flow into the perforating arteries adjacent to the aneurysm lumen.

When the aneurysms are at vessel bifurcations, several modifications of the endoluminal conformal sleeve can be used for treatment. In one embodiment of the present invention, the endoluminal conformal sleeve is made Y-shaped.

Alternatively, the endoluminal conformal sleeve can be in the shape of a funnel.

For purposes of the present invention, the term "endovascular thin film device" refers to all of the shape memory or in situ polymerizable devices used to repair aneurysms, irrespective of the shape of the aneurysm or the vessel(s) associated therewith.

In yet another embodiment of the present invention, shape memory or photopolymerizable coils can be used as an intravascular occlusion device.

BRIEF DESCRIPTION OF THE DRAWINGS

FIG. 15A shows the native state of a wide neck bifurcation aneurysm.

FIG. 15B shows the deploying state for an endovascular thin film device in the form of an endoluminal conformal polymer funnel in a wide neck bifurcation aneurysm.

FIG. 15C shows the deployed state of the endovascular thin film device in a wide neck bifurcation aneurysm.

FIGS. 16A–16D show an endovascular thin film device in the form of a shape memory aneurysm occlusion device constructed of a single thin film membrane.

FIG. 18A–18D show an endovascular thin film device in the form of a shape memory aneurysm occlusion device constructed of overlapping thin film membranes with hollow delivery guidewire.

DETAILED DESCRIPTION OF THE EMBODIMENTS

Figure 1:
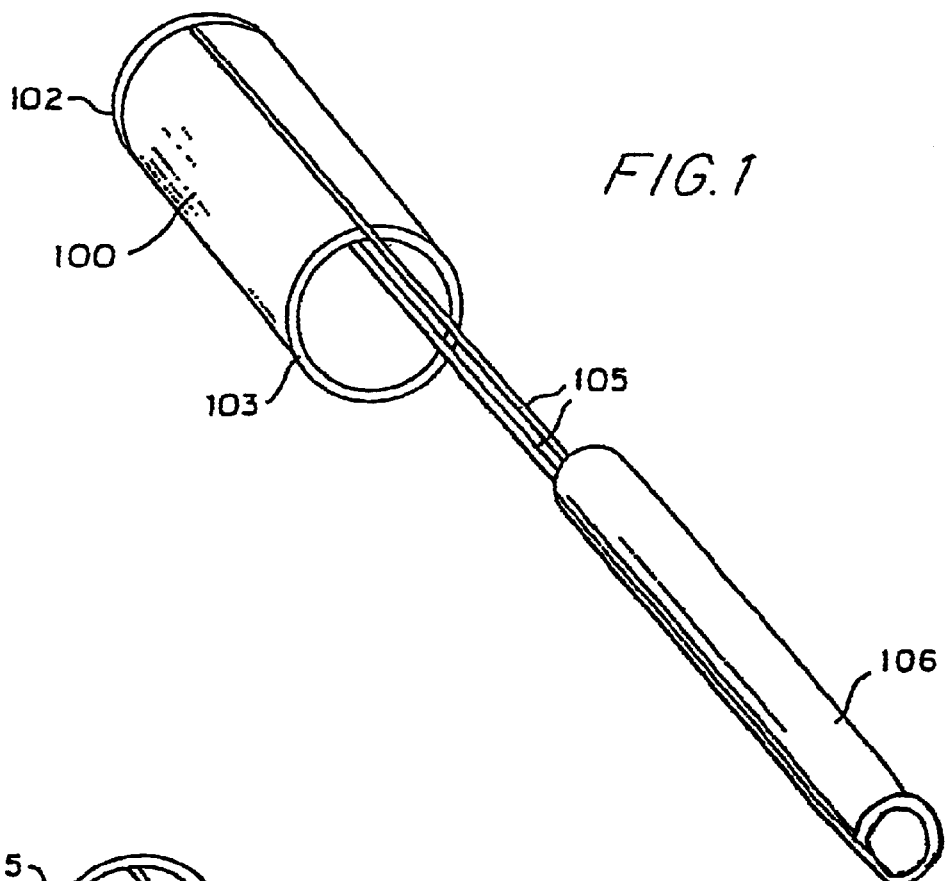
FIG. 1 shows an endovascular thin film device in the form of a shape memory alloy thin film sleeve in the deployed state.

The present invention provides endovascular thin film devices which are useful in treating and preventing stroke, including ischemic stroke caused by a blood clot in a blood vessel in the brain or hemorrhagic stroke caused by aneurysmal subarachnoid hemorrhage. These devices can also be used to restore patency and otherwise treat other areas of the body, such as the trachea, esophagus, colon, and extracranial vessels, etc.

The endovascular thin film devices according to the present invention can be produced in a variety of configurations for treating ischemic and hemorrhagic stroke.

The thin film device can be in the form of an endoluminal sleeve for treating sidewall aneurysm configurations, well dissection and fusiform aneurysms, as well as focal areas of atherosclerosis via endoluminal reconstruction. The thin film sleeve can be constructed of a thin film of a shape memory alloy, or of a monomer and catalyst mixture encased in a biocompatible envelope. The thin film sleeve is bounded by a proximal and distal collapsible ring configured on an optionally detachable delivery platform.

The thin film sleeve may be segmented to improve positioning along a vessel curvature. The inter-segmental attachment configuration is optimized to provide the best fit with the local angio-architecture. The attachment configurations include linear, helical, or double helical attachments.

The thin film sleeve may be in a Y configuration for treating bifurcation saccular aneurysms. Alternatively, the thin film sleeve may be in a rolled sleeve configuration with optional locking tabs.

The thin film sleeve may be a partial sleeve, which may have one or more rings. The rings may be open or in an overlapping configuration. The partial sleeve presents a surface of aneurysm neck closure to be positioned over the orifice of the aneurysm entrance in the parent vessel. The rings secure the device in place within the parent vessel.

All of the above sleeve configurations can be fenestrated, partially fenestrated, or completely fenestrated.

The thin film sleeve can be configured as a fenestrated closed sleeve attached to a proximal collapsible ring to create a distal embolus prevention device. The closed sleeve configuration can be bounded by a proximal collapsible ring or multiple attachment struts in a parachute configuration to create a clot retriever.

In another configuration, the distal collapsible ring is significantly larger in diameter than the proximal collapsible ring, which creates a funnel shape. This configuration makes it possible to treat bifurcation saccular aneurysms by intra-aneurysmal occlusion. Flow through the proximal ring can be controlled via a one-way valve to introduce a variety of aneurysm volume-filling materials, including coils, polymers, and hydrogels.

The present invention also includes thin film aneurysm occlusion devices. In one embodiment, the thin film aneurysm device is in the shape of a hemisphere. The hemisphere may be composed of a single membrane or multiple overlapping membranes. Each hemisphere may have a delivery platform that it solid or hollow.

In another embodiment, the aneurysm occlusion device comprises a thin film sphere with a proximal solid membrane and a distal fenestrated membrane. This device may have a solid delivery platform or a hollow delivery platform.

All of the thin film aneurysm occlusion devices can incorporate an intrinsic aneurysm volume-filling material or may allow the introduction of extraneous aneurysm volume-filling materials. The hollow delivery platform may have an optional one-way valve for admitting this volume-filling material. The devices can be either detachable or implantable for aneurysm exclusion, or may be non-implantable devices for endovascular aneurysm neck remodeling during treatment.

When the thin film devices are made of shape memory alloy, the shape memory can be controlled by infusing low temperature liquid within the delivery system.

Materials for the Endovascular Thin Film Devices

Since the endovascular thin film devices will function as an endovascular implant, mechanical compatibility between the device and the host vessel is critical. The materials used in designing the devices will resemble as closely as possible the mechanical characteristics of the vessel lumen. If there are large differences in mechanical properties between natural tissues and artificial materials, concentrations of high stress and strain appear at attachment sites, which may lead to material failure and subsequent malfunction of the implant. Optimal mechanical properties of an implant material can be specified only if there is adequate knowledge of the tissues with which it comes in contact.

The mismatch caused by the differences in mechanical properties between vascular grafts and host arteries yields local stress concentrations and flow disturbances which might result in tearing of the host artery, local thrombus formation, and other complications. These problems are fatal, particularly for small-diameter grafts. Clinical experience and chronic animal experiments on arterial grafts have indicated that there is a fairly good correlation between their compliance (elasticity) and patency rate. A higher patency rate is obtained for materials which have matching compliance to the host artery. These results emphasize that the mechanical compatibility of materials has an important role in the graft performance, and materials used for vascular grafts should be sufficiently elastic and flexible to retain normal hemodynamics and strong and durable enough to resist over-extension and fatigue failure.

The present invention provides endovascular thin film devices in a variety of materials to match the mechanical characteristics of the host vessel.

In one embodiment, biocompatible thin films created from materials with shape memory and superelasticity are used to form the endovascular thin film device. These materials undergo a phase transformation in their crystal structure when cooled from the strong, high-temperature form (Austenite) to the weaker, low-temperature form (Martensite). This phase transformation, which is inherent within the material, is the basis for the unique properties of these materials.

These desirable properties include shape memory and superelasticity. When a shape memory alloy is in its Martensitic form, it is easily deformed to a new shape. However, when the alloy is heated through its transformation temperatures, it reverts to Austenite and recovers its previous shape with great force. This process is known as shape memory (Perkins et al, in *Engineering Aspects of Shape Memory Alloys*, Duerig et al (eds.), Butterworth-Heinemann, pp. 195–206, 1990). Various investigators have shown that the temperature at which the alloy remembers its high-temperature form can be adjusted by slight changes in alloy composition. These unique alloys also show a superelastic behavior if deformed at a temperature which is slightly above their transformation temperatures. This effect is caused by the stress-induced formation of some Martensite above its normal temperature. Because it has been formed above its normal temperature, the Martensite reverts immediately to undeformed Austenite as soon as the stress is removed. This quality provides a rubber-like elastic property in these alloys.

When nickel titanium is used as the shape memory alloy, the Martensite state is fairly weak and undergoes deformation at stresses of 10,000–20,000 psi. In addition, in the Martensite state the alloy is able to absorb up to 8% recoverable strain (Yinong et al, *Acta Metallurgica* 38:1321–1326, 1990) In the stronger Austenite state, the deformation stress rises to 35,000–100,000 psi. In both forms of the alloy, elongation to failure occurs at over 25% and tensile strength is up to 200,000 psi. The proven biocompatibility and extreme corrosion resistance of this material make it highly suitable for use in medical devices (Caslteman et al, in *Biocompatibility of Clinical Implant Materials*, Vol. 1, Williams (ed.), CRC Press, pp. 129–154, 1981).

Over the past several years various investigators have refined the process for producing shape memory alloys in the form of thin films. It has been shown that films of nickel-titanium alloy can be deposited onto a variety of substrates in a wide range of thicknesses. Such films have been produced in thicknesses that range from 2000 Ångstroms to 50 microns on a variety of substrates, including silicone. The resulting material, when released from its substrate, exhibits shape recovery characteristics similar to those of bulk nitinol as described above. These thin films can be electrically actuated to shift from one state to another. Alternatively, the superelastic properties of nitinol can be used advantageously in the creation of thin film devices for medical devices.

The shape memory metal alloy compositions which can be used in the present invention constitute conventionally-known blends and specially formulated metallic mixtures of nickel and titanium or mixtures of other metals which undergo a phase transition, i.e., a molecular rearrangement of atoms, molecules, or ions within a lattice structure due to a temperature change. The unique capability of shape memory alloys is that these alloys change shape or configuration as a direct consequence of a change in temperature. The alloy composition "remembers" its earlier and specifically prepared shape because the phase change affects its structure on the atomic level only, without disturbing the arrangement of the molecules which would otherwise be irreversible.

When these shape memory alloys are intentionally superheated far above their transition temperature (either electrically or by externally applied heat), a stretched temperature-transformed alloy form results which contracts and exerts considerable force. The temperature-transformed alloy composition becomes memory-shaped in a fixed specific configuration. Afterwards, when cooled to below its transition temperature, the alloy composition can then be bent and shaped into other configurations while retaining the fixed "memory" of the particular shape in the earlier superheated condition. Thus, these shape memory alloy compositions are recognized as being both deformable and thermoelastic, as well as being able to revert to a prepared memory-shaped configuration as a consequence of being warmed to a temperature above its individual transition temperature.

Shape memory alloys are used in a great variety of medical applications. At least twenty different formulations of these alloys are conventionally known to exhibit the shape-memory effect and property, with all of the conventional alloys comprising different mixtures of nickel and titanium in varying percentage ratios (*Design News*, Jun. 21, 1993 issue, pages 73–76). For example, a range of different shape memory alloy wires are commercially available in diameters from 0.001 to 0.10 inches from Dynalloy Inc, of Irvine, Calif. In addition, surgical anchors having superelastic properties and formed by two or more arcs of wire strands, which can withstand strains exceeding 10%, have been developed by Mitek Surgical Products, Inc. of Norwood, Mass. Also, blood clot filters formed of shape memory alloy wires are commercially sold for implantation in large blood vessels, such as the vena cava, by Nitinol Medical Technologies, Inc., of Boston, Mass. While these commercially-available products illustrate the use of one or more shape memory alloy formulations by the manufacture of their particular articles, a more general listing of conventionally-known properties and characteristics for shape memory alloy compositions can be found in Kim, U.S. Pat. No. 5,797,920, the entire contents of which are hereby incorporated by reference.

All of the different specific formulations and metallic blends which are biocompatible and which yield a deformable, thermoelastic, shape memory alloy composition are suitable for use in the present invention. All of the shape memory alloys rely on a crystal phase change from a higher temperature Austenite form to a lower temperature Martensite form to accomplish the memory effect. The cubic Austenite phase behaves much like ordinary metals as it deforms. In contrast, the complex crystal Martensite form can be found by reversible movement of twin boundaries to change the average "tilt" or strain in each segment of the alloy. The overall strain can be eliminated by releasing the stress, by maintaining it if it is not thermally stable (the superelastic effect), or by heating the alloy to change it back to Austenite form (shape memory effect).

The crystal transformation of shape memory alloy composition is, by definition, thermoelastic. That is, it progresses in one direction on cooling below the transition temperature and in the other direction upon heating above the transition temperature. The amount of transformation change versus temperature, measured either as the percent of Martensite form or the strain in a constantly stressed element, is a function of and can be plotted against temperature (° C.) directly. The change from one phase (and identifiable shape) to another typically occurs in a narrow temperature range (often 5–10° C.). Hysteresis takes place before the reverse transformation occurs.

The amount of strain accommodated due to the movement of twin boundaries differs in each metallic alloy blending system. In the nickel-titanium system, for example, up to 8% reversible tensile strain is available. However, to guarantee a long life use, the strain is often limited to 4–5%.

The stress-strain behavior of shape memory alloy compositions is employed to help explain the shape memory effect. For instance, Martensite is much easier to deform than Austenite. Therefore, one can deform the alloy while cold with much less force than when heated to change it back to the Austenite form. As a result, the alloy converts thermal energy to mechanical work at high forces.

To prepare and fix the desired shape to be remembered when the alloy undergoes a temperature phase transition, the alloy composition must be superheated initially to about 500° C. (roughly 930° F.) for one hour while held in the fixed shape and position to be memorized. During the superheating process, the native alloy blend enters what is called the Austenite phase—a rigid lattice of nickel atoms surrounded by titanium alloys. Then, as the alloy metal cools below its transition temperature (which varies with the percentage proportion of nickel), the alloy composition adopts the Martensite phase, in which the nickel and titanium atoms assume a very different arrangement, one that is very easy to bend and deform. Subsequently, when the deformed metallic alloy is reheated to the chosen transition temperature range between about 25 and 35° C., thermal motion causes the atoms to snap back into the Austenite phase, thereby restoring the fixed memory-shaped configuration of the object.

For producing endovascular thin film devices and other devices in vivo according to the present invention, it is most desirable that the shape memory alloy composition be prepared in a metallic blend and formulation such that the temperature transition phase occurs at a temperature less than about 35° C. but greater than about 25° C., and preferably in the range of from about 30–35° C. This preferred transition phase temperature range is dictated by the demands of the human body, which maintains a normal temperature of about 37° C. (98.6° F.), and typically shows a normal temperature range and varies by one or two degrees Celsius above and/or below this normative temperature standard. It is for this reason that the broad temperature range be about 25–35° C. and the preferred temperature transition occur in the range of 30–35° C. However, to ensure a safety margin of medical usefulness, the transformation into the intended and fixed memory-shaped configuration should occur at least by a temperature of 35° C.

A preferred form of shape memory metal is made from sputtered nickel titanium alloy, because these sputtered alloys have unique and enabling properties. These properties allow the design and manufacture of medical devices for use in small and tortuous spaces, particularly for use in the intracranial circulation. Preferred thickness for the shape memory metal is from about 0.5 to about 150 microns, with a most preferred thickness of about 2 to 50 microns.

Sputtered titanium nickel film is a unique material which is significantly different from bulk nitinol, which is conventionally used in these types of devices. Bulk nitinol is always in an ordered crystal structure from the moment of its creation. In contrast thereto, sputtered TiNi film, when it is deposited, has an amorphous, chaotic and disordered microcrystalline structure. Sputtered TiNi film can be made as thin as 2 microns with a three-dimensional crystal lattice structure on the order of one micron. Bulk nitinol, on the other hand, has a crystal lattice structure of 150 microns, thus limiting its crystal domain to two dimensions when it is in a thickness less than 150 microns. It is this structural constraint that limits the tensile properties, superelastic properties, and the shape memory properties of bulk nitinol when it is rolled and acid etched to a thickness below approximately 50 microns. Using proprietary sputter deposition techniques, such as those disclosed in U.S. Pat. No. 5,016,914 to Busch et al, the entire contents of which are hereby incorporated by reference, TiNi endovascular thin film devices can be produced which are well below 50 microns in thickness but which retain all of the structural characteristics of bulk nitinol and exhibit remarkable shape memory properties, thus enabling the creation of micro devices for entirely novel medical applications.

In another embodiment, the device is constructed from a highly-elastic synthetic polymeric material encased in a biocompatible envelope. Among suitable materials are:

(1) a segmented microporous poly(ether urethane) synthesized from 4,4'-diphenylmethane diisocyanate (MDA), polytetramethylene glycol (PTMG), and polyethylene oxide-polydimethylsiloxane-polyethylene oxide (PES);

(2) Cooley low-porosity woven Dacron graft;

(3) Cooley double velour knitted Dacron graft; and (4) Gore-Tex thin-walled extended PTFE graft.

These biocompatible materials, or other suitable biocompatible materials, resemble the stress-strain relationships and tensile properties of the host arteries. The tensile strength of a calf s thoracic aorta is in the range of 100 gm/mm$^2$. Compliant polyurethane vascular graft material has been developed by Hayashi et al (*J. Bio. Mater. Res.: Applied Biomaterials* 23(A2):229–244, 1989) that closely approximates this tensile strength. The stiffness parameters of the polyurethane vascular grafts compare favorably with the stiffness characteristics of excised human femoral arteries and are in between those of excised human carotid and coronary arteries. Most of the commercially available vascular graft materials that are now in clinical use vary significantly from the stiffness characteristics of the host arteries.

The biocompatible envelope of the present invention is constructed of a compliant elastic material that has mechanical characteristics similar to those of the host vessel. In addition, the biocompatible envelope has a thickness of approximately 0.2 mm to approximately 0.8 mm. The monomer and catalyst mixture which are to undergo polymerization are contained within the leaves of the envelope. Additionally, the biocompatible envelope is preferably impregnated with antithrombogenic material to reduce the likelihood of in situ thrombosis after deployment.

In one embodiment, the polymer-forming network is a photosensitive acrylate, and visible laser or ultraviolet radiation is used to initiate polymerization. In a preferred embodiment, radiation is delivered to the sleeve via a cladded optic fiber. Photopolymerization of the sleeve occurs via intimate juxtaposition of unclad fiber optic filaments incorporated within the thin film envelope and the acrylate photosensitive mixture of initiators and monomers contained within. This results in the formation and curing of the endoluminal sleeve in situ. After activation, the device conforms to the endoluminal contour of the vessel and maintains its conformal shape. The activated endoluminal sleeve is then detached from its delivery platform, and the microcatheter and delivery platform are removed.

A number of polymers have been found to be biocompatible and can be polymerized in situ to form conformal endoluminal sleeves. The criterion for the polymers to be used to form endovascular thin film devices according to the present invention is that the polymer precursor be fluid or sufficiently pliable at room temperature so that it can be introduced to the site in a biocompatible envelope configuration as described above, and that it be capable of polymerization in situ to form a conformal endoluminal sleeve which is biocompatible. The type of precursor that can be used for this purpose is not restricted to any one type of precursor, nor to any type of polymerization initiator. That is, any precursor that can be introduced to the site to be treated and polymerized in situ to form a biocompatible polymer can be used. The polymerization initiator can be any type of polymerization initiator that can be used to form a polymer from the precursor. Such initiators include, but are not limited to, radiation, including visible, infrared and ultraviolet light, X-radiation, heat energy, sonic energy, etc. Where appropriate, the initiator can be a chemical catalyst which is incorporated in the precursor and is activated, such as by pressure, mixing, heat, etc., shortly before or when the precursor is introduced to the desired spot for polymerization to occur.

Acrylate polymers are but one example of such a polymer material which can be formed in situ from a precursor. It has been shown that the mechanical properties of acrylate networks formed by visible laser-induced polymerization, as well as TV light-induced polymerization, can be altered as a function of the initial molecular composition of the reacting mixture (Torres-Filho et al, 1994). Additionally, elastic characteristics may be added to the polymer network by copolymerizing a flexible acrylate oligomer with the networking monomers. In particular, the addition of nylon 6,6 can be an effective means of improving the elastic properties of the polymer network, thus making it more compatible for endovascular implants. In the photopolymerization process, liquid monomers and oligomers are mixed with photoinitiators and co-initiators and a solid, network polymer structure is formed rapidly upon irradiation.

Other examples of photopolymerizable, biocompatible polymers include polyethylene glycol tetraacrylate, which can be photopolymerized with an argon laser under biologically compatible conditions using an initiator, such as triethanolamine, N-vinylpyrrolidone, and eosin Y. Similar photopolymerizable macromers having a poly(ethylene glycol) central block extended with hydrolyzable oligomers, such as oligo(D,L-lactic acid) or oligo(glycolic acid) and terminated with acrylate groups may also be used. Other suitable polymers can be obtained by reference to *The Polymer Handbook*, 3rd Ed. (Wiley, N.Y., 1989), the entire contents of which are incorporated herein.

Conventionally, liquid acrylic monomers and oligomers are mixed with photoinitiators and co-initiators and a solid, network polymer structure is rapidly formed upon irradiation. The most commonly used radiation sources are ultraviolet light and visible light.

Fluorone dyes have successfully been used, together with amino co-initiators, as efficient free-radical sources for the polymerization of monomers containing double bonds, including acrylic, vinylic, and allylic double bond systems.

The mechanical properties of the polymers used can be affected by structural modifications in the network. Among the various structural modifying factors include:

(1) the presence of peroxides in the monomer mixture;

(2) the amount and type of diacrylate oligomer added to initiate the multifunctional acrylate mixture;

(3) ionizable dyes, depending on the initial acidity of the medium;

(4) the presence of micrometric inorganic fillers which optionally had their surface treated with silane coupling agents containing polymerizable groups, such as vinyl or methacrylic.

Among non-limiting examples of monomers and oligomers that can be used to form the endoluminal conformal sleeves of the present invention are:

(1) polyethylene glycol-400, diacrylate PEGA-400;

(2) trimethylol propane triacrylate (TMPTA);

(3) dipentaerythritol pentaacrylate (DPHPA);

(4) polybutadiene diacrylate (PBUA);

(5) acrylated aliphatic urethane (PUA).

Dyes which can be used as photoinitiators for the polymers are exemplified by the following, which list is not exhaustive:

(1) 2,4-diiodo-6-butoxy-3-fluorone (DIBF);

(2) 2,4,5,7'tetraiodo fluorone (TIHF);

(3) 2,7-di-t-butyl(4,5-diiodo) fluorone (DBDIHF);

(4) 9-cyano-(2,4,5,7-tetraiodo)fluorone (CNTIHF).

Optional co-initiators, such as electron donors, include, but are not limited to, amines, such as N,N-dimethyl-2,6-diisopropylamine and N-phenylglycine.

In the non-deployed state, the thin film device in the form of an endoluminal conformal sleeve consists of a soft and collapsible biocompatible envelope which effectively contains the precursor. The envelope is bounded by distal and proximal collapsible rings attached to a detachable guidewire delivery system. The collapsible rings and guidewire delivery system are constructed of a highly elastic and radiopaque material that has shape memory. A preferred material for this is sputtered nickel-titanium allow. As the conformal sleeve is extruded from the catheter, the proximal and distal 900 loops are deployed and the sleeve assumes its preset cylindrical configuration. The monomer is then polymerized by imposition of an initiating force or chemical, which force is introduced through the fiber optic sleeve, or which chemical is present in the precursor. The chemical may be one that is activated by a force introduced through the fiber optic sleeve. The material properties of the deployed endoluminal implant resemble the elasticity and tensile characteristics of the host vessel within the physiological pressure range of 60–160 mm of Hg. The preselected size of the conformal sleeve should be such that the diameter fits snugly within the parent vessel and the length effectively excludes the region of aneurysmal weakness from the circulation.

As noted above, the polymers used to form the device sleeve must be mechanically compatible with the host vessel. One method of testing the mechanical compatibility of the polymers is by testing tensile strength. Such tests can be conducted at ambient temperature (about 23° C. with no strict humidity control), using photopolymerized dogbone-shaped samples. These are performed using an L-500 instrument (Lloyd Instruments, Fareham, England), fitted with an NLC-500N load cell. The crosshead speed used is 5.0 mm/s, the sample gauge length is 70.0 mm, and the width is 6.0 mm.

The instrument is controlled by an MCM-4135T Goldstar PC booted with Lloyd's DAPMAT software. This data analysis program allowed direct observation of the load x elongation behavior of the sample during the test. After the test ended, it also automatically displayed various physical parameters of interest, including stress at break (N-mm$^2$) and elongation at break (absolute, in mm, and relative, in %), maximum load (N), work performed (N.mm) and Young's modulus of elasticity (N.mm$^2$), among others. Thus, one skilled in the art can readily determine if a given polymer has the mechanical characteristics of the vessel to be occluded, without undue experimentation.

Thin Film Sleeve

In this embodiment, an endovascular thin film device in the form of a sleeve is provided for endoluminal reconstruction of a vessel segment. FIG. 1 shows an endovascular thin film device in the form of a shape memory alloy thin film endoluminal sleeve 100 in the deployed state. A distal collapsible ring 102 and a proximal collapsible ring 103 are used to sit and position the sleeve in the vessel to be repaired. Detachable deployment wires 105 hold the sleeve in a microcatheter 106 for delivery.

Figure 2:
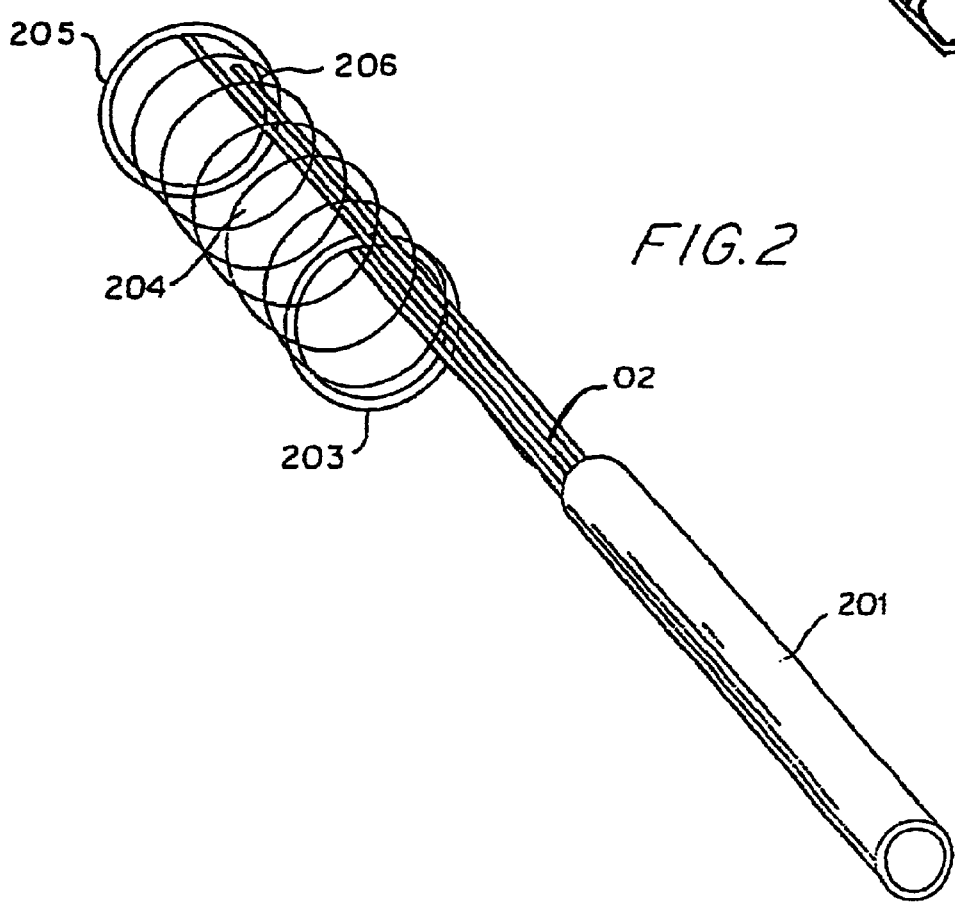
FIG. 2 shows an endovascular thin film device in the form of an endoluminal conformal polymer sleeve in the deployed state.

FIG. 2 shows an endovascular thin film device as an endoluminal conformal sleeve prior to being polymerized in situ. The material for forming the sleeve is encased in a biocompatible envelope 204, which is delivered by surrounding the envelope with a distal collapsible ring 205 and a proximal collapsible ring 203 through a microcatheter 201. Detachable deployment wires 202 retain the rings in place prior to polymerization. A fiber optic filament 206 may be delivered along with the detachable deployment wires to direct suitable initiating stimulus to polymerize the precursor to form the conformal endoluminal sleeve.

Figure 5:
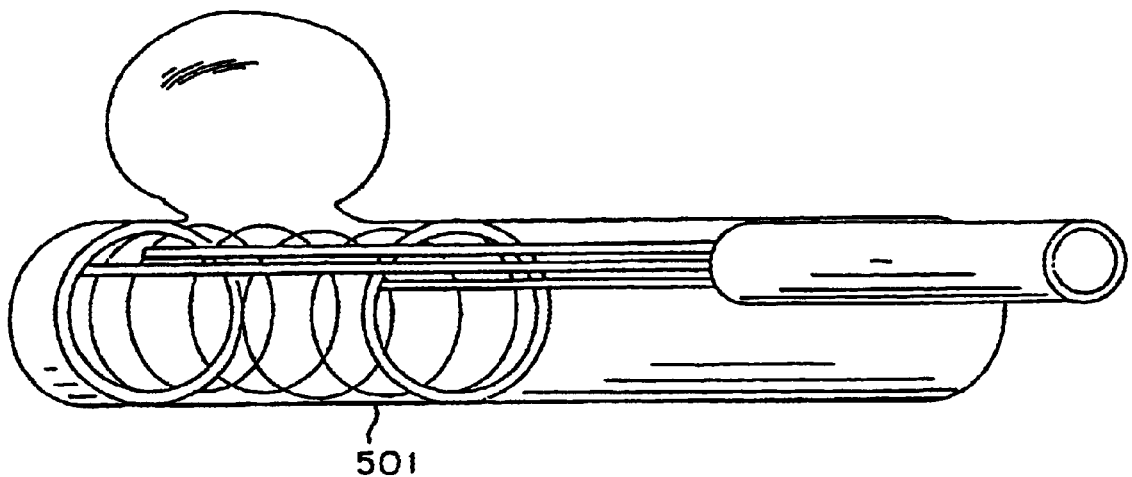
FIG. 5 shows an endovascular thin film device in the form of a segmented shape memory alloy thin film sleeve in vivo.

The endovascular thin film device in the form of conformal sleeves can be made of any type of suitable thin film, preferably a very thin shape memory alloy thin film sleeve. FIG. 5 shows a segmented shape memory alloy thin film sleeve 501 in vivo. Segmentation can be optimized to best capture the shape of the vessel.

Fenestrated Thin Film Sleeve

Once the endovascular thin film device is deployed within the parent vessel, the region of aneurysmal weakness is reinforced by the presence of the device. However, there is a circumferential endoluminal lining that is caused by the placement of the device which may interfere with perfusion of adjacent perforating arteries or vascular branches. In this situation, a device in the form of a fenestrated endoluminal sleeve is indicated; the fenestrations allow blood flow into the perforating arteries adjacent to the aneurysm lumen. With the fenestrated sleeve in place, catheterization of the aneurysm lumen through the fenestrations within the sleeve can be accomplished to perform endovascular occlusion of the aneurysm lumen with coils.

Partial, non-circumferential fenestration of the sleeve may be useful in order to permit perfusion through adjacent branches of vessels while occluding the orifice of the aneurysmal sac.

FIG. 15 shows a fenestrated segmented SMA thin film sleeve bounded by a distal and proximal collapsible ring. Fenestrations allow on-going blood flow into perforated arteries. Segmentation allows conformal placement within curved vascular segments. Intrasegmental attachments may be in any pattern that will permit optimal placement around a curvature, such as a linear or helical pattern.

Figure 4:
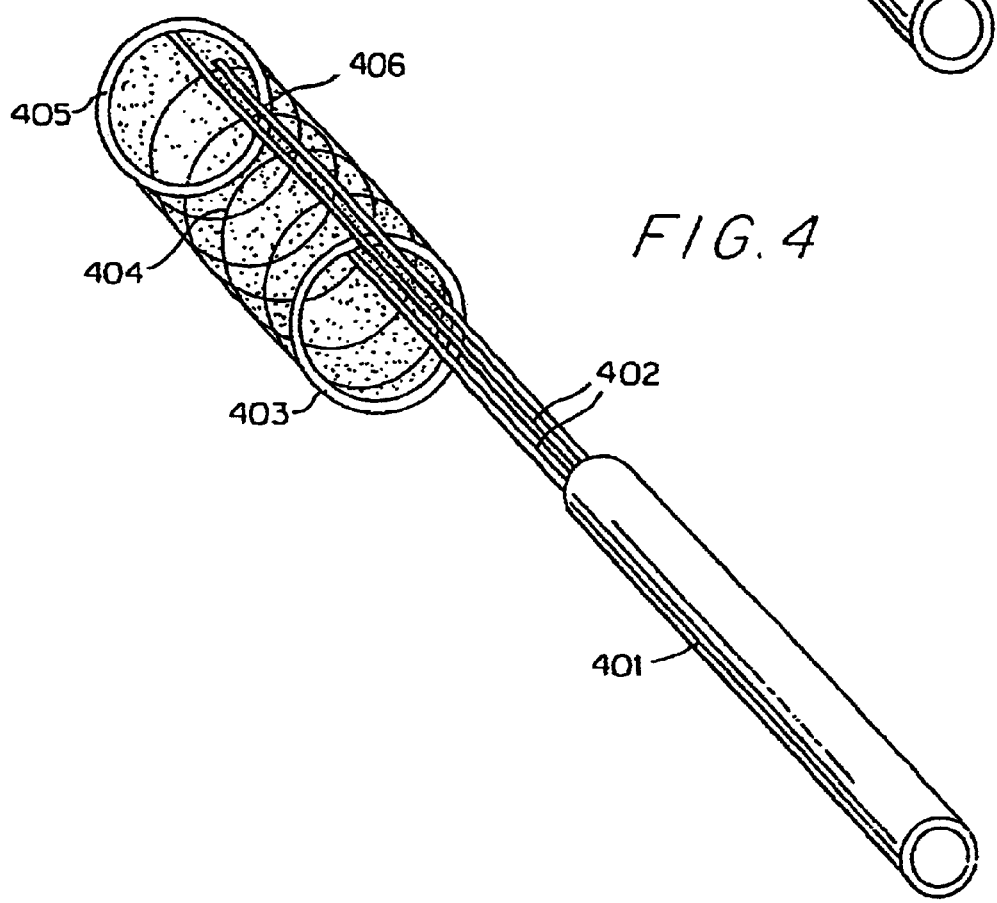
FIG. 4 shows an endovascular thin film device in the form of a fenestrated endoluminal conformal polymer sleeve in the deployed state.

FIG. 4 shows an endovascular thin film device in the form of a fenestrated endoluminal conformal sleeve in the deployed state. The material for forming the sleeve is encased in a biocompatible envelope 404, which is delivered by surrounding the envelope with a distal collapsible ring 405 and a proximal collapsible ring 403 through a microcatheter 401. Detachable deployment wires 402 retain the rings in place prior to polymerization. A fiber optic filament 406 may be delivered along with the detachable deployment wires to direct suitable initiation energy to polymerize the precursor and form the conformal endoluminal sleeve.

Thin Film Rolled Sleeve With Optional Intralocking Tabs

Figure 3:
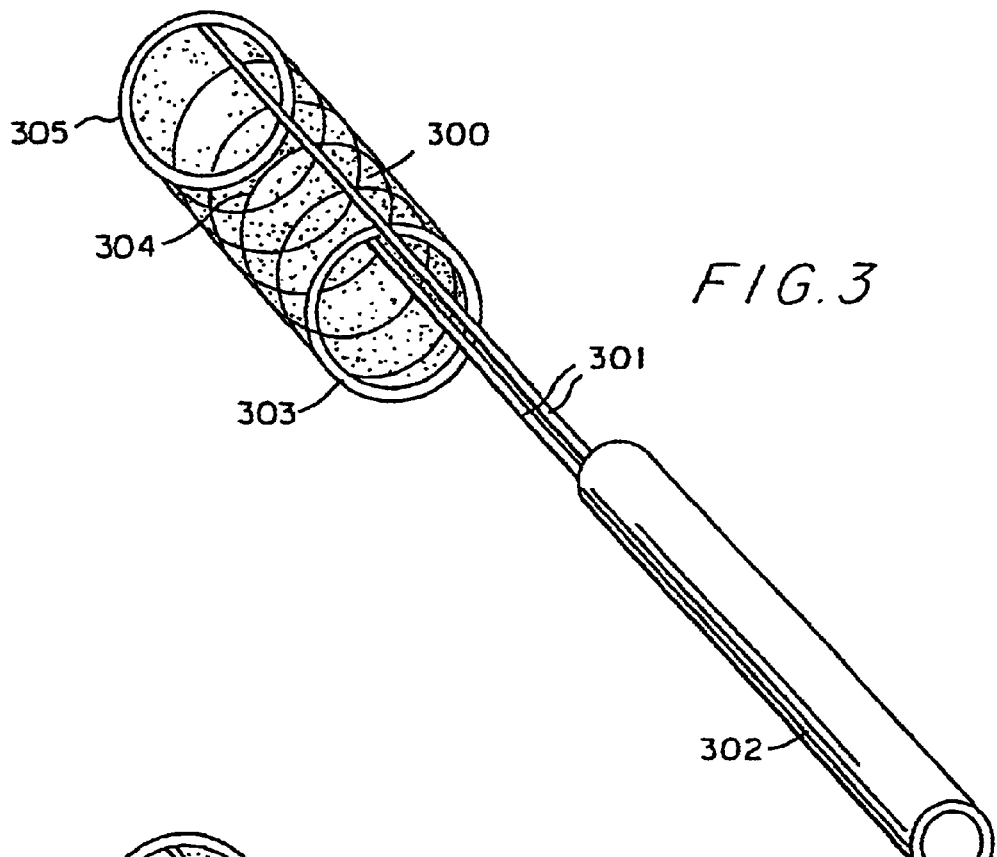
FIG. 3 shows an endovascular thin film device in the form of a fenestrated segmented shape memory alloy thin film sleeve device in the deployed state.
Figure 7:
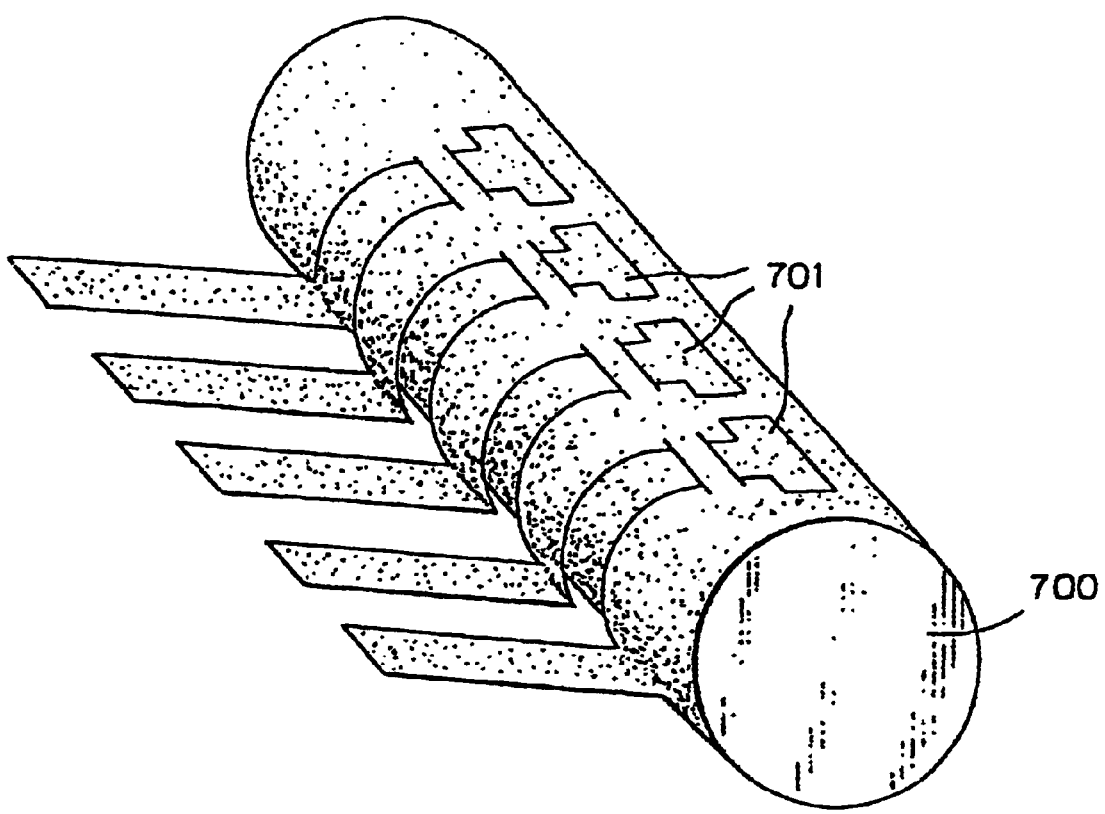
FIG. 7 shows an endovascular thin film device in the form of a fenestrated SMA thin film rolled sleeve in the deployed state outside vessel constraints.

In this embodiment, shown in FIG. 7, an endovascular thin film device in the form of a fenestrated thin film rolled sleeve 700 is shown in the deployed state outside of vessel constraints. The fenestrated thin film sleeve 700 is provided with optional locking tabs 701, such that it can be rolled to a small diameter configuration around a mandrel or sheathed catheter 302, as shown in FIG. 3, and introduced into a small diameter blood vessel. When the sleeve has reached the site of deployment, the constraining sheath is removed or the mandrel is pushed out, allowing the rolled sleeve configuration to unravel, thereby conforming to the luminal diameter of the blood vessel in situ.

Partial Thin Film Sleeve

Figure 8:
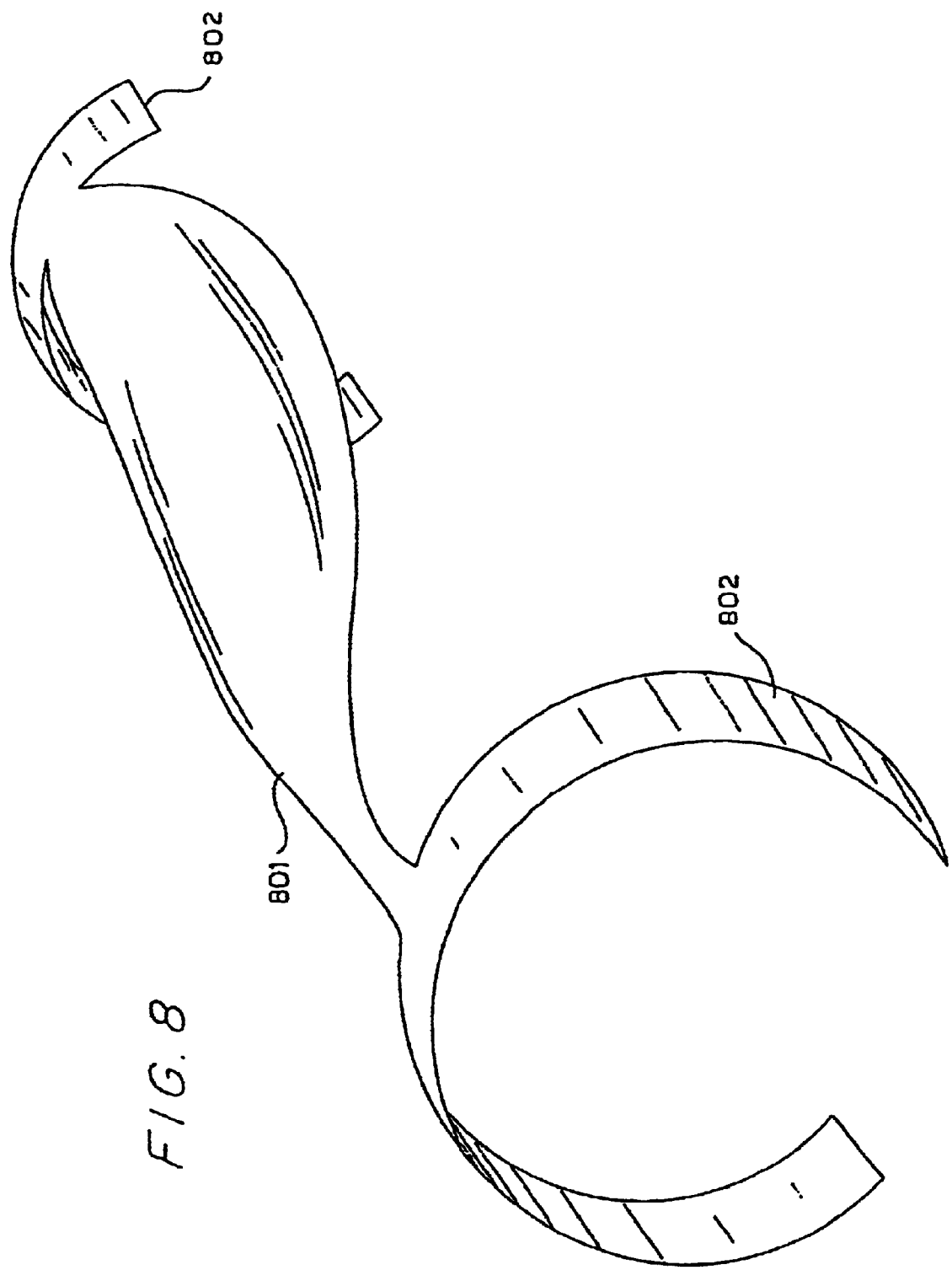
FIG. 8 shows an endovascular thin film device in the form of a partial thin film sleeve.
Figure 9:
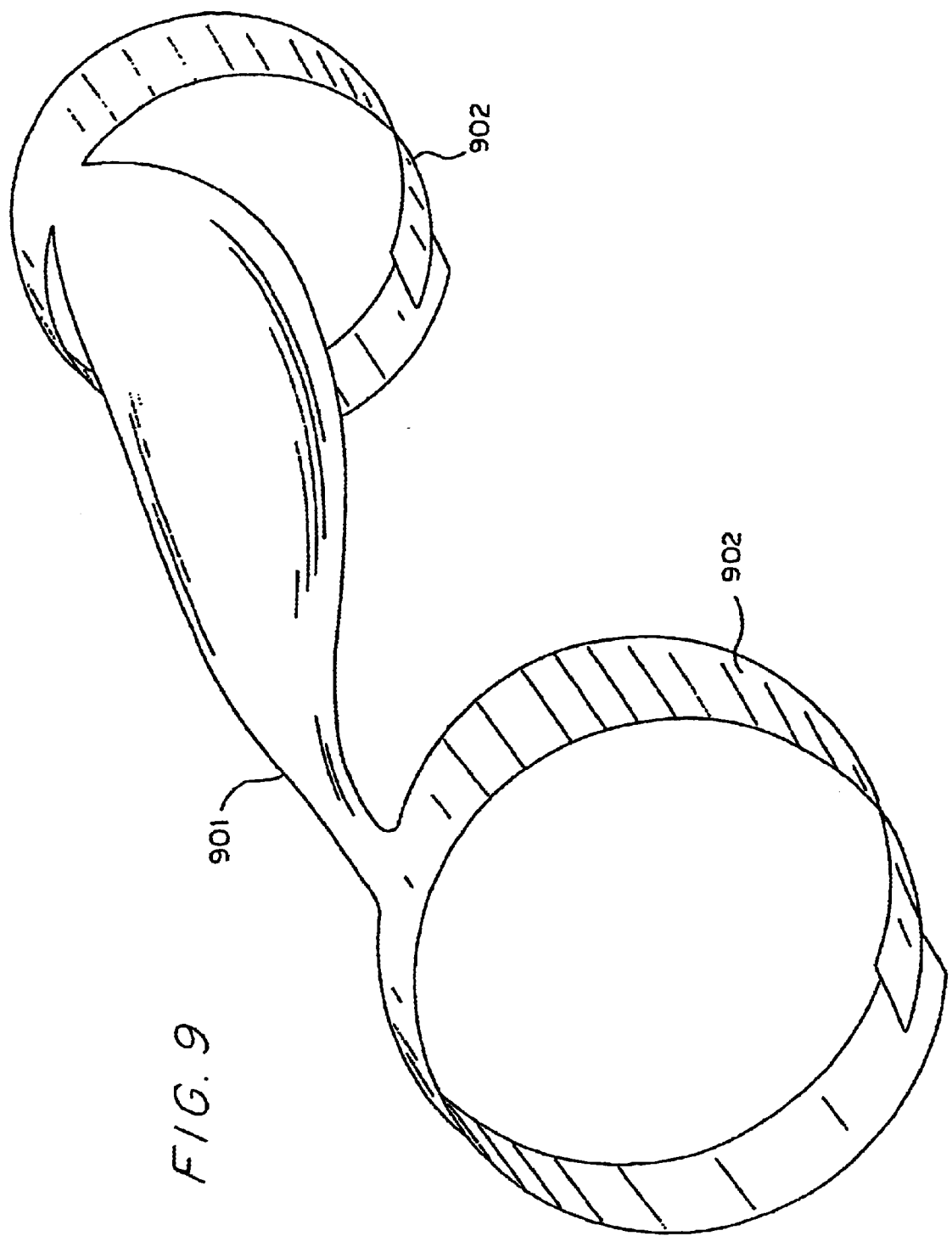
FIG. 9 shows an endovascular thin film device in the form of a partial thin film sleeve with overlapping rings.
Figure 10:
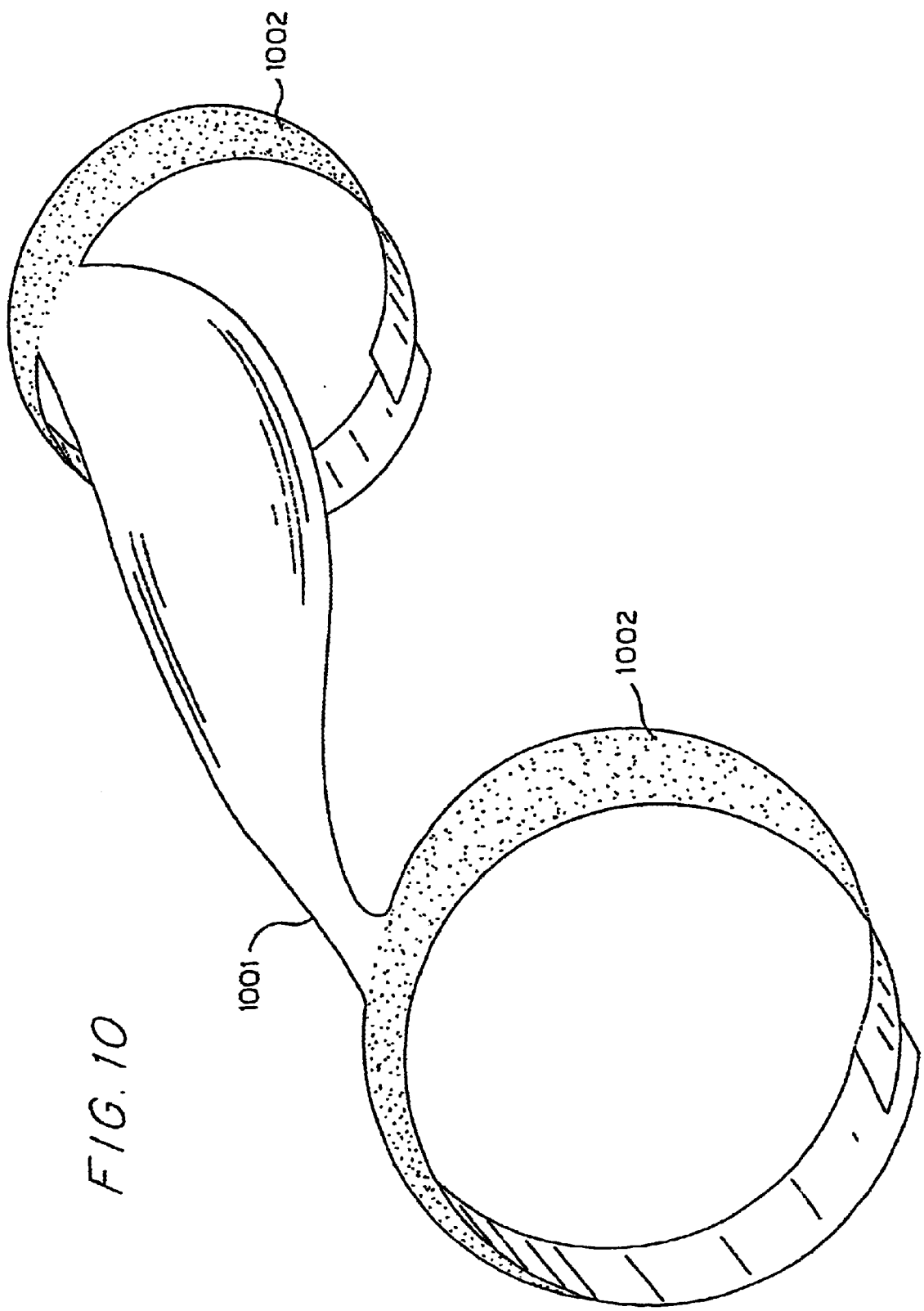
FIG. 10 shows an endovascular thin film device in the form of a fenestrated partial thin film sleeve formed by overlapping rings.

The thin film sleeve can also be in the form of a partial sleeve. FIG. 8 shows a partial thin film sleeve made from open rings of shape memory thin film 802 surrounding an aneurysm neck closure surface 801. FIG. 9 shows overlapping thin film rings 902 surrounding an aneurysm neck closure surface 901. FIG. 10 shows a fenestrated partial thin film sleeve comprising overlapping rings 1002 surrounding an aneurysm neck closure surface 1001.

Thin Film Distal Protection Device: Fenestrated Endoluminal Conformal Closed Sleeve During a variety of open surgical and percutaneous endovascular procedures, including angioplasty, stent deployment, aneurysm occlusion, and bypass revascularization, there is a clinical need to protect the distal vasculature from thrombo-emboli while simultaneously allowing on-going perfusion of the distal vascular bed. In this embodiment, shown in FIG. 3, an endovascular thin film device is provided in the form of a shape memory fenestrated closed sleeve 300 which is mounted on an introducing microguidewire assembly, including a deployment microguidewire 301 and a microcatheter 302. The fenestrated endoluminal conformal closed sleeve 300 is a pliable and collapsible device constructed using a thin film shape memory material that is delivered via a microcatheter 302 into the vessel lumen distal to the operative site. There it is deployed and undergoes a shape memory phase transformation to assume the stable configuration of a closed-end endoluminal fenestrated "wind sock." The fenestrations within the thin film allow for on-going distal perfusion regardless of the time required for the operative procedure. This pliable fenestrated closed-end sleeve is bounded at its proximal end by a proximal collapsible ring 304 and, optionally, at its distal end by the tapering closed "toe" of the "sock." The fenestrations of the thin film mesh are on the order of microns in size in order to trap particulate emboli and prevent distal embolization.

Clot Retriever: Fenestrated Endoluminal Conformal Closed Sleeve

Recent clinical data suggest that in patients with acute occlusion of intracranial arteries, rapid removal of the intra-arterial clot can be effective in improving outcome. Until now, intracranial clot removal has been primarily accomplished by anticoagulation and thrombolysis. There are several disadvantages in this method of clot removal. First, the clot composition in many patients makes thrombolysis using urokinase or TPA not feasible. Second, if clot lysis is successful, the problem of reperfusion hemorrhage within the distal vascular bed is dramatically magnified due to the patient's anticoagulated condition at the time of reperfusion hemorrhage due to prior administration of thrombolytics and heparin. Third, removal of clot by lysis is much more likely to result in distal embolization of small blood clots in a vascular territory that is at the end arteriorlar level and is beyond the help of collateral circulation from adjacent vessels. Because of these shortcomings, an ideal clot removal system would involve mechanical removal of the blood clot from the intracranial vessel without disruption of the patient's coagulation cascade.

Figures 12A, 12B:
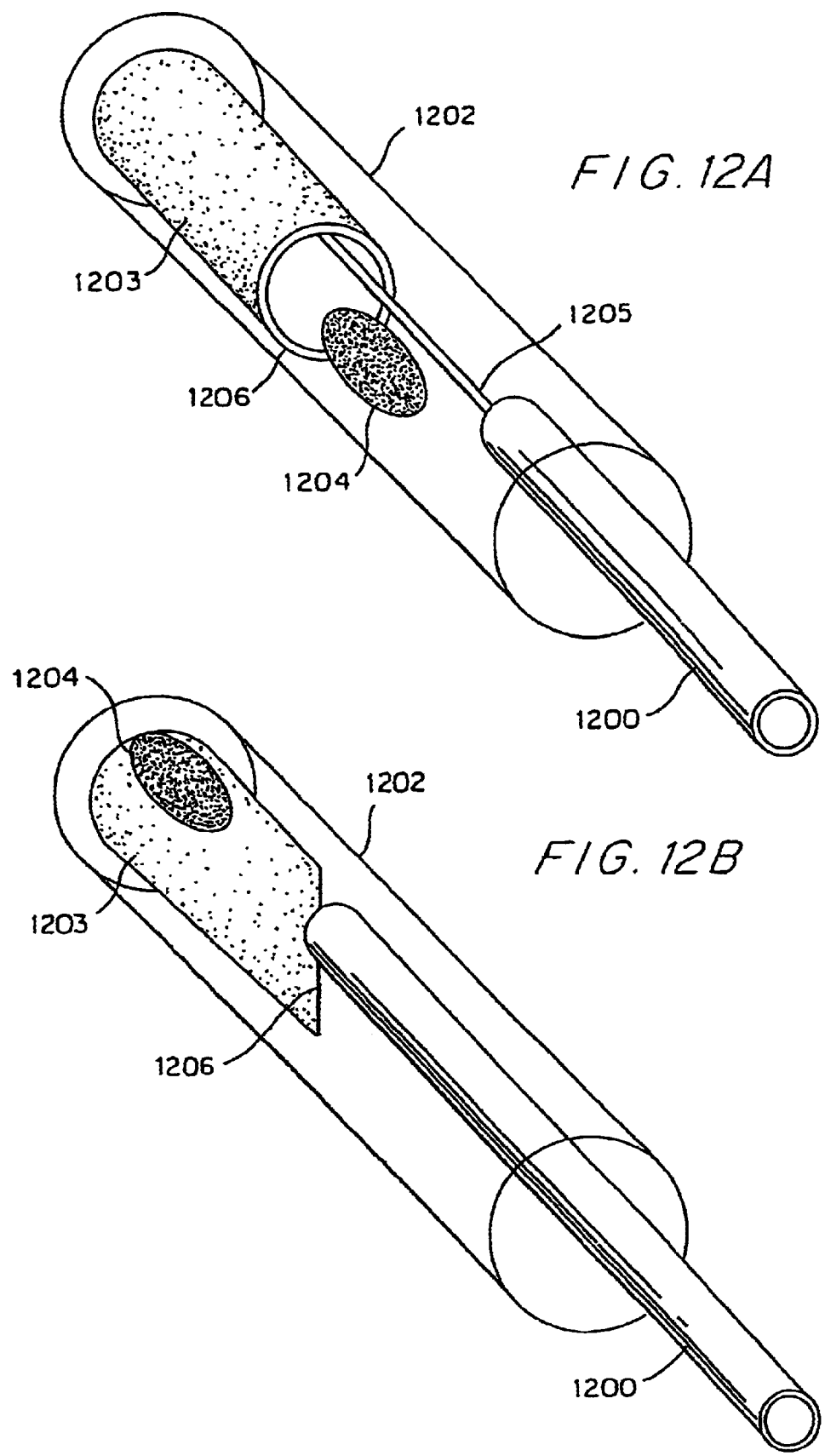
FIG. 12A shows an endovascular thin film device in the form of a clot retriever and its deployment method.
FIG. 12B shows the device of FIG. 12A withdrawn through an occluded blood vessel segment to meet the microcatheter tip.

As shown in FIGS. 12A and 12B, the present invention provides technology to cross the occluded blood vessel segment with microcatheters 1200 and microguidewires 1001. In this embodiment of the endovascular thin film device, after crossing the occluded vascular segment 1202 with a microcatheter 1200, the thin film clot retriever 1203 is introduced through the microcatheter distal to the blood clot 1204 in a region of the cerebral vasculature that has absent or minimal blood flow. In the open (FIG. 12A) or deployed condition (FIG. 12B) the clot retriever 1203 is withdrawn through the clotted segment of intracranial vessel from a distal to a proximal location. This withdrawing mechanism encapsulates the blood clot 1204 within the fenestrated closed sleeve 1205. As the clot retriever device is brought back to meet the more proximal location of the microcatheter, the union of the clot retriever and the microcatheter closes the proximal collapsible ring 1206 or the draw struts of the clot retriever, thus entrapping the blood clot 1204 within the clot retriever and allowing its safe removal from the vasculature through a larger diameter guiding catheter located proximal to the position of the microcatheter and clot retriever. At the end of the procedure, when distal protection from emboli is no longer required, the microcatheter is advanced over the introducing microguidewire 1205 to a point just beyond the proximal collapsible ring 1204 such that the open end of the "sock" is cinched closed, thereby trapping the particulate emboli within the closed "sock." The endoluminal closed sleeve and microcatheter assembly can then be retracted as a unit into the guiding catheter and safely removed from the patient.

Figure 13A:
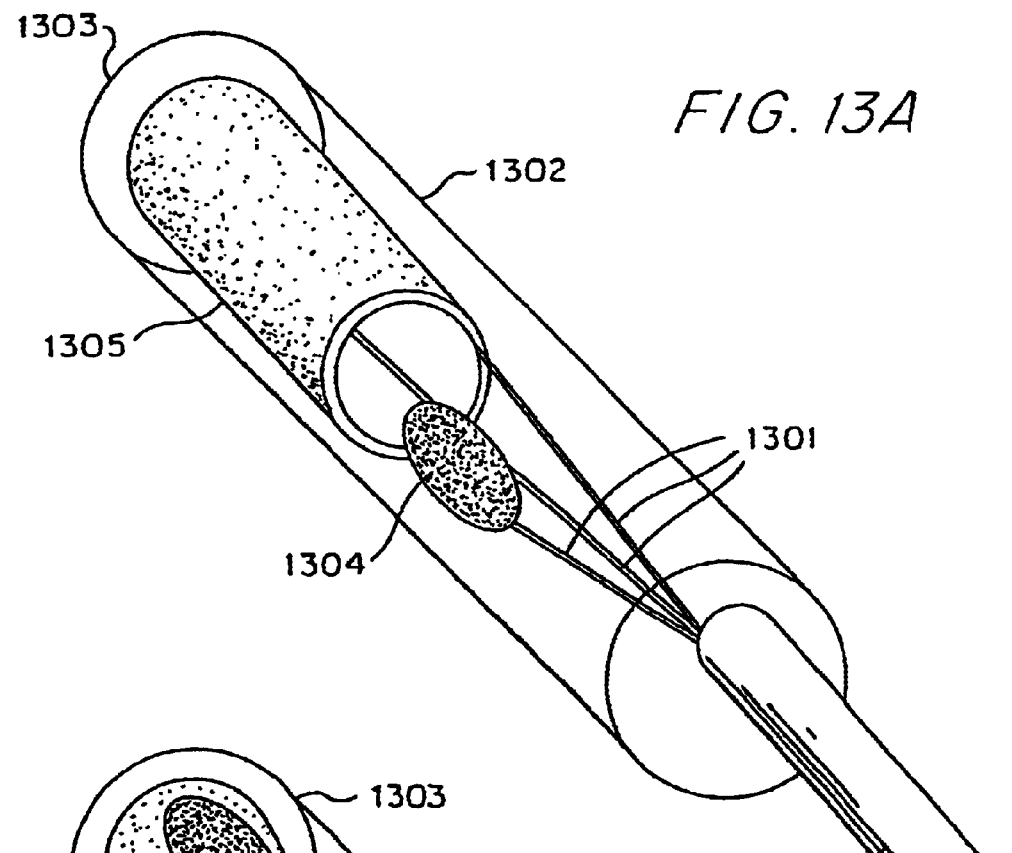
FIGS. 13A and 13B show an endovascular thin film device in the form of a clot retriever in a parachute is configuration.
Figure 13B:
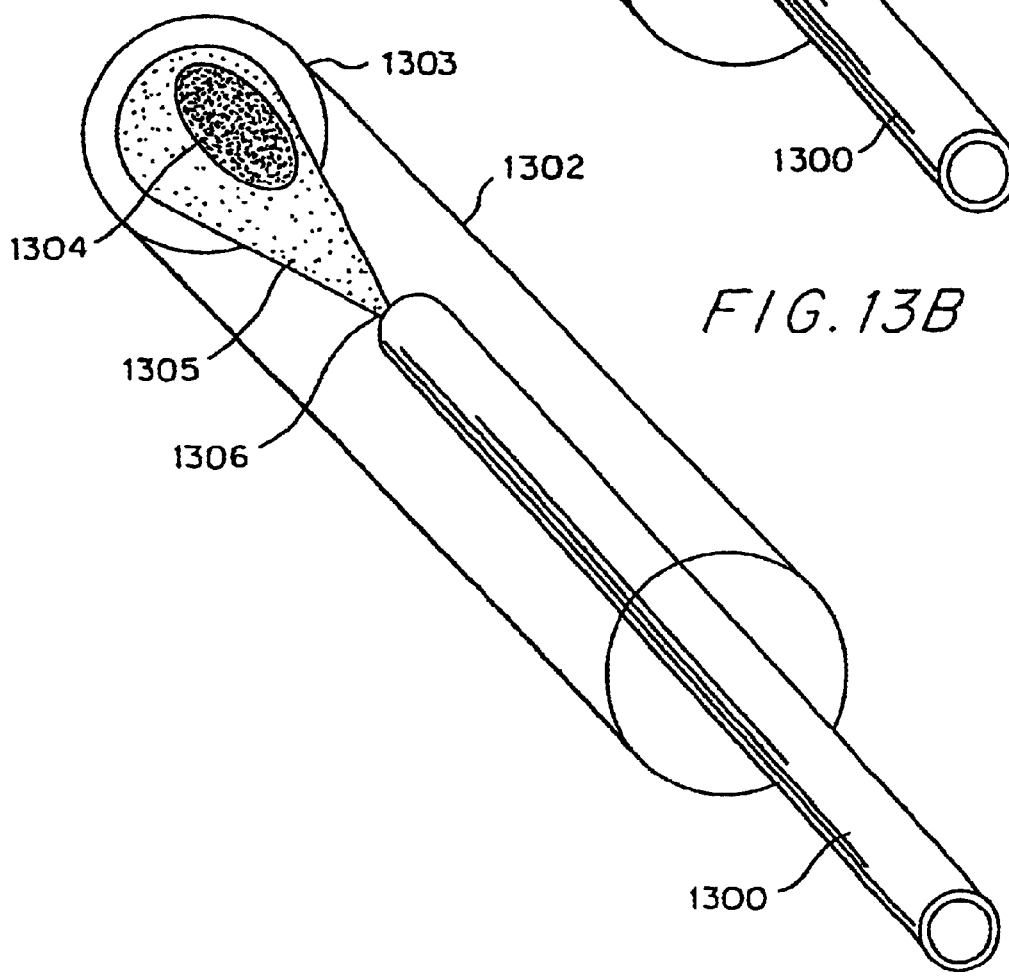

FIGS. 13A and 13B show another embodiment of an endovascular thin film device in the form of a clot retriever in parachute configuration. In this embodiment, after crossing the occluded vascular segment 1302 with a microcatheter, 1300, the thin film clot retriever 1303 is introduced through the microcatheter distal to the blood clot 1304 in a region of the cerebral vasculature that has absent or minimal blood flow. In the open (FIG. 13A) or deployed (FIG. 13B) condition, the clot retriever 1303 is withdrawn through the clotted segment of intracranial vessel from a distal to a proximal location. This withdrawing mechanism encapsulates the blood clot 1304 within the fenestrated closed sleeve 1305. As the clot retriever device is brought back to meet the more proximal location of the microcatheter, the union of the clot retriever and the microcatheter closes the retriever around the blood clot, allowing its safe removal from the vasculature through a larger diameter guiding catheter located proximal to the position of the microcatheter and clot retriever.

Endoluminal Y-Sleeve

Where the aneurysm is a bifurcation aneurysm, the endoluminal conformal sleeve device can be modified as needed. When aneurysms occur at a vessel bifurcation, blood flow must be present in the proximal vessel, as well as in the distal branch vessels beyond the bifurcation. In order to preserve this flow while still occluding the aneurysm neck and excluding the aneurysm lumen from the circulation, an endovascular thin film device in the form of a Y-shaped endoluminal sleeve can be deployed, directing blood flow from the proximal vessel into the distal branch vessels beyond the bifurcation, while at the same time excluding the aneurysm lumen from the circulation.

Figure 6:
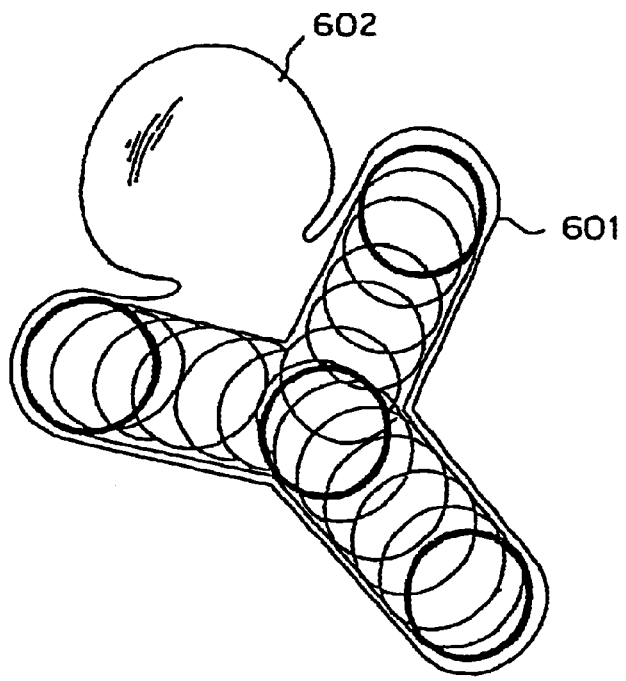
FIG. 6 shows an endovascular thin film device in the form of a bifurcated Y-sleeve deployed within a bifurcation aneurysm.

FIG. 6 illustrates an endoluminal Y-sleeve 601 in place within a bifurcation aneurysm 602.

Funnel Shape Intra-aneurysmal Occlusion Device

The endoluminal conformal sleeve device can also be modified to a funnel shape to treat bifurcation aneurysms In this configuration, the distal collapsible ring is of significantly larger diameter (approximately up to about 20 times larger) than the proximal collapsible ring. In order to deploy the conformal funnel, the aneurysm lumen is catheterized and the conformal funnel is extruded from the catheter. The configuration of the funnel is such that the larger distal collapsible ring is somewhat larger than the neck of a wide neck bifurcation aneurysm. The proximal collapsible ring is similar in size to the diameter of the microcatheter. Once deployed, the endoluminal conformal funnel is polymerized or shape memory actuated in situ such that the funnel is seated within the wide neck aneurysm. In order to assure that the funnel does not turn, or migrate distally into the lumen of the aneurysm, polymer coils, platinum coils, or other types of aneurysm occlusion devices are extruded through the funnel to fill the aneurysm volume. The coil-filled aneurysm exerts a radial tension on the funnel, thus maintaining the stable position of the funnel and holding it securely against the neck of the aneurysm. The end of the extruding coil fits snugly within the proximal collapsible ring and seals the aneurysm lumen, thus excluding it from the circulation while maintaining preservation of blood flow within the parent vessel.

The funnel is preferably made of a shape memory material in the form of a thin film. The thin film funnel can be actuated to shift from one state to the other.

Figure 17A:
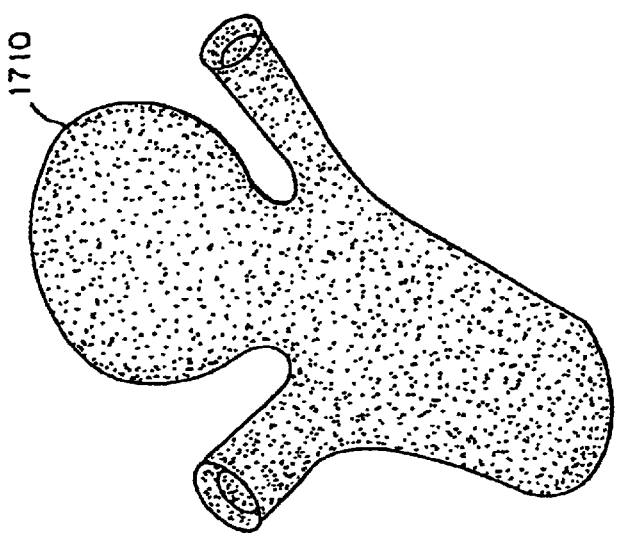
FIGS. 17A–17D show an endovascular thin film device in the form of a shape memory aneurysm occlusion device constructed of overlapping thin film membranes with solid delivery guidewire.
Figure 17B:
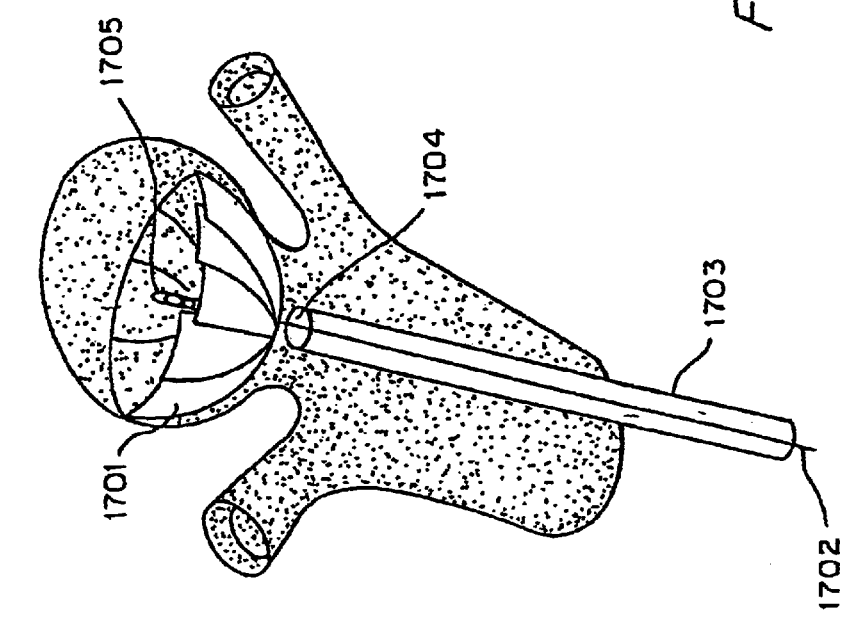

FIG. 17A shows a wide neck bifurcation aneurysm 1710. FIG. 17B shows an endovascular thin film device in the form of a shape memory alloy aneurysm occlusion device constructed of overlapping thin film membranes 1701. FIG. 17B shows the deploying state where the device is mounted on a solid delivery guidewire 1702 and extruded from a microcatheter 1703. The overlapping membranes of the segmented aneurysm occlusion device unfold upon extrusion from the microcatheter. Within the concavity of the segmented hemisphere there is compacted shape memory material 1705.

Figure 17C:
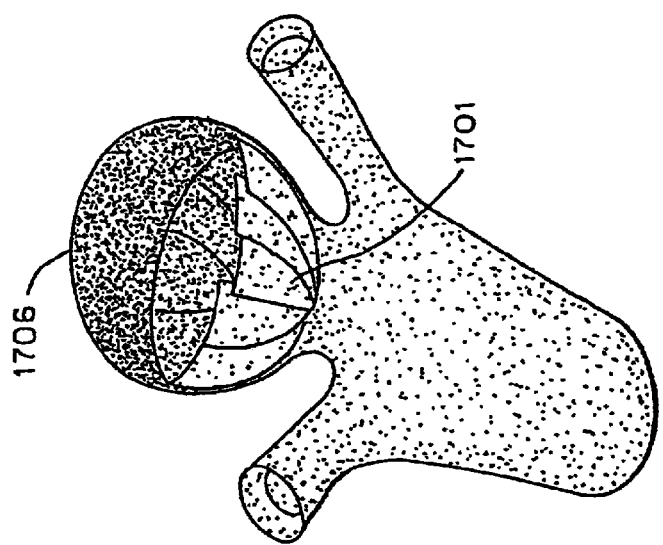

FIG. 17C shows the deployed state of the device after a triggering stimulus has caused the shape memory material to unravel 1706, filling the aneurysm volume, and holding the segmented hemisphere 1701 in place. After the aneurysm occlusion device position is secured, the device is detached from its solid delivery guidewire 1702 at a detachment zone 1704.

Figure 17D:
Figure 19C:
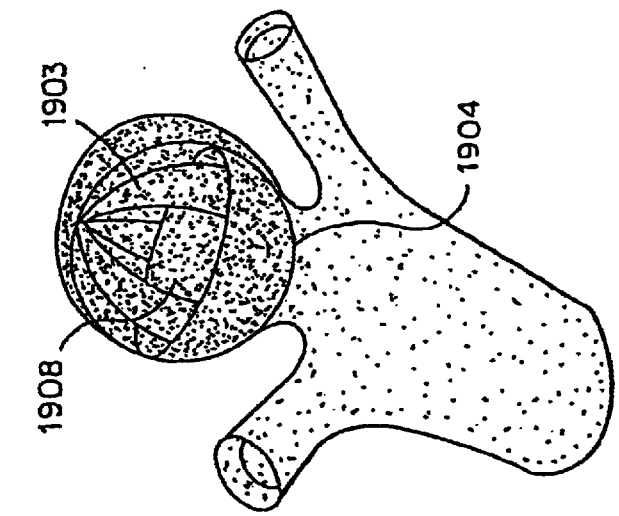
FIGS. 19A–19D show a shape memory alloy endovascular thin film device constructed of a single membrane.
Figure 19B:
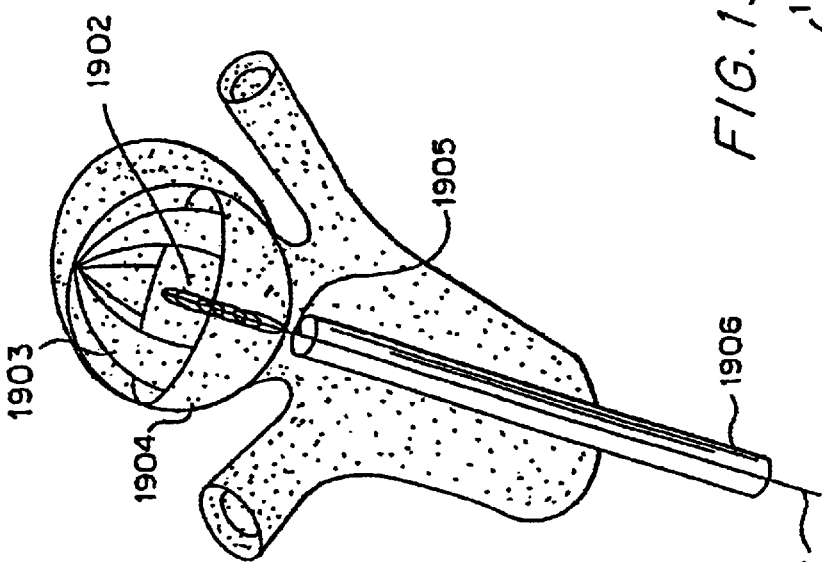
Figure 19D:
Figure 19A:
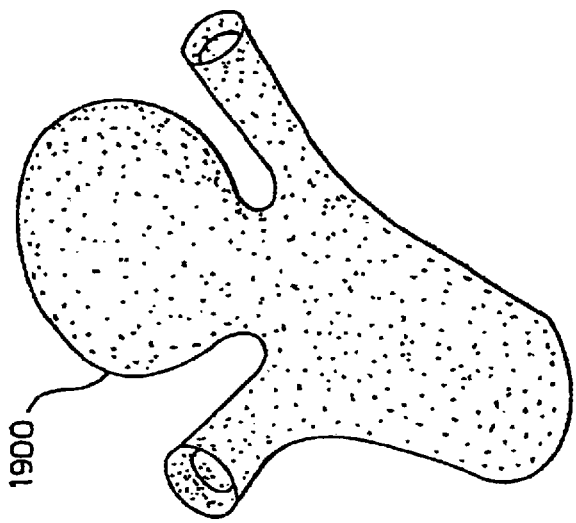

FIG. 17D shows the undeployed state of the aneurysm occlusion device. In the collapsed and folded state, the device profile is such that it can be introduced into an aneurysm lumen through a microcatheter.

FIG. 18A shows a wide neck bifurcation aneurysm 1810 in its native state. FIG. 18B shows an endovascular thin film device in the form of a shape memory alloy segmented hemisphere constructed of overlapping thin film membranes 1801 mounted on a hollow delivery guidewire 1802. FIG. 18B shows the deploying state where the device is extruded from the microcatheter 1803 and unfolds within the aneurysm 1810 to occlude the orifice of the aneurysm lumen. Subsequently, through the hollow delivery guidewire 1802, coils or other aneurysm occlusion devices 1804 are introduced to fill the aneurysm volume and thereby exert a radial force on the segmented hemisphere holding it in place.

FIG. 18C shows the deployed state of the device 1801 after occlusion of the aneurysm volume and detachment from the hollow delivery guidewire. The aneurysm volume 1818 is filled with coils or hydrogel, etc.

FIG. 18D shows the undeployed state of the shape memory alloy segmented hemisphere. In the collapsed and folded state, the device profile is such that it can be introduced into the aneurysm lumen through a microcatheter.

FIG. 19 shows a shape memory alloy thin film sphere aneurysm occlusion device constructed of a single membrane. A wide neck bifurcation aneurysm 1900 is shown in its native state in FIG. 19A. FIG. 19B shows the deploying state, including a fenestrated membrane distal hemisphere 1903 and a solid membrane proximal hemisphere in which is enclosed compacted shape memory material 1902. A detachment zone is provided at 1905 where the device is detached from the solid delivery guidewire 1907 through the microcatheter 1906. FIG. 19C shows the deployed state of the device in which unraveled shape memory material 1908 fills the aneurysm volume. Polymerizable coils can be part of the endovascular thin film device of the present invention. These coils have a central core consisting of two filaments: one fiber optic filament for transmission of initiator energy and another filament that has properties of shape memory, such as platinum or nitinol. This core is covered by a monomer-catalyst mixture that can undergo polymerization upon exposure to an initiator transmitted via the central fiber optic filament. The coil is encased in a thin biocompatible membrane. In its primary configuration, the coil has a diameter of 0.001–0.1 cm and a variable length in the range of 1–40 cm. In its secondary configuration, a complex shape is assumed within the vessel or aneurysm lumen, and this shape is maintained after polymerization.

Thin Film Endovascular Funnel

Figure 14C:
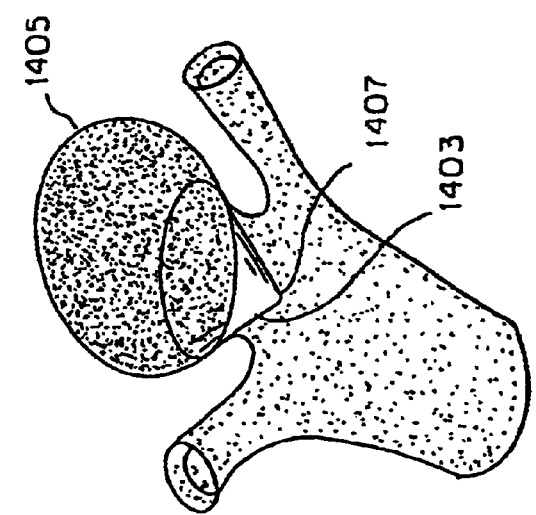
FIGS. 14A–14C show a shape memory alloy endovascular thin film device in the form of a thin film funnel.
Figure 14B:
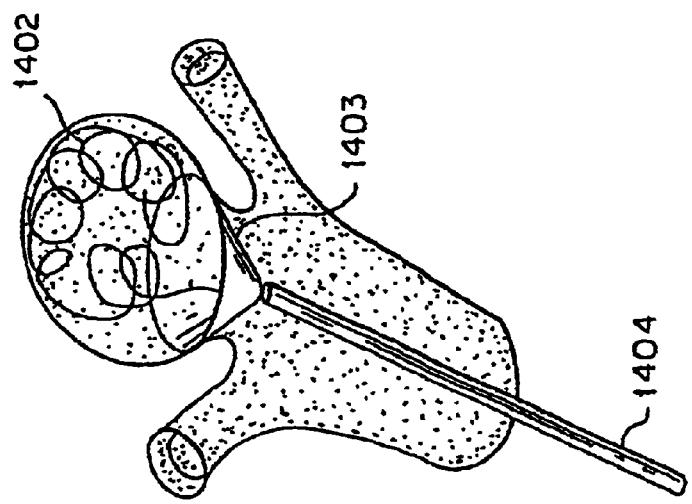
Figure 14A:
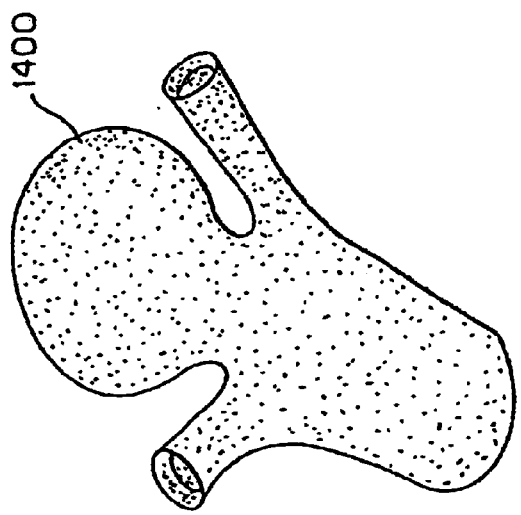

FIGS. 14A–14D show a shape memory alloy endovascular thin film device in the form of a thin film funnel. In FIG. 14A, a wide neck bifurcation aneurysm in its native state is shown at 1400. In the deploying state, the extruding coil or hydrogel 1402 is in a compacted state. The shape memory alloy thin film funnel 1403 is attached to a microcatheter 1406 for delivery through the microcatheter 1406. In the deployed state, shown in FIG. 14C, the coils or hydrogel material 1405 fills the aneurysm volume. A closed one-way valve 1407 retains the coils or hydrogel within the aneurysm volume.

FIG. 15A shows a wide neck bifurcation aneurysm in the native state 1501. FIG. 15B shows positioning of an endovascular thin film device in the form of an endoluminal conformal polymer funnel 1503 within the bifurcation aneurysm 1501. An extruding polymer coil 1504 is carried by a microcatheter to the aneurysm. FIG. 15C shows the endoluminal conformal polymer funnel 1507 in the deployed state in which the aneurysm volume 1501 is filled with polymer coils 1505, and the bottom of the aneurysm is closed off with a polymer plug 1506 at the bottom of the endoluminal conformal funnel 1507.

Thin Film Aneurysm Occlusion Devices

FIGS. 16A–16D show an endovascular thin film aneurysm occlusion device in the form of a shape memory alloy occlusion device constructed of a single thin film membrane 1601. FIG. 16B shows the deploying state in which the device is mounted on a solid delivery guidewire 1602 and extruded from the microcatheter 1603. Within the concavity of the hemisphere there is a segment of compacted shape memory material 1604.

FIG. 16C demonstrates the deployed state of the device after a triggering stimulus has caused unraveling of the shape memory material filling the aneurysm volume and holding the hemispheric device in place. After the aneurysm occlusion device position is secure, the device is detached from its solid delivery guidewire.

FIG. 16D shows the undeployed state of the shape memory alloy aneurysm occlusion device. In the collapsed and folded state, the device profile is such that it can be introduced into the aneurysm lumen through a microcatheter.

Distal Embolism Prevention Devices

Figure 11:
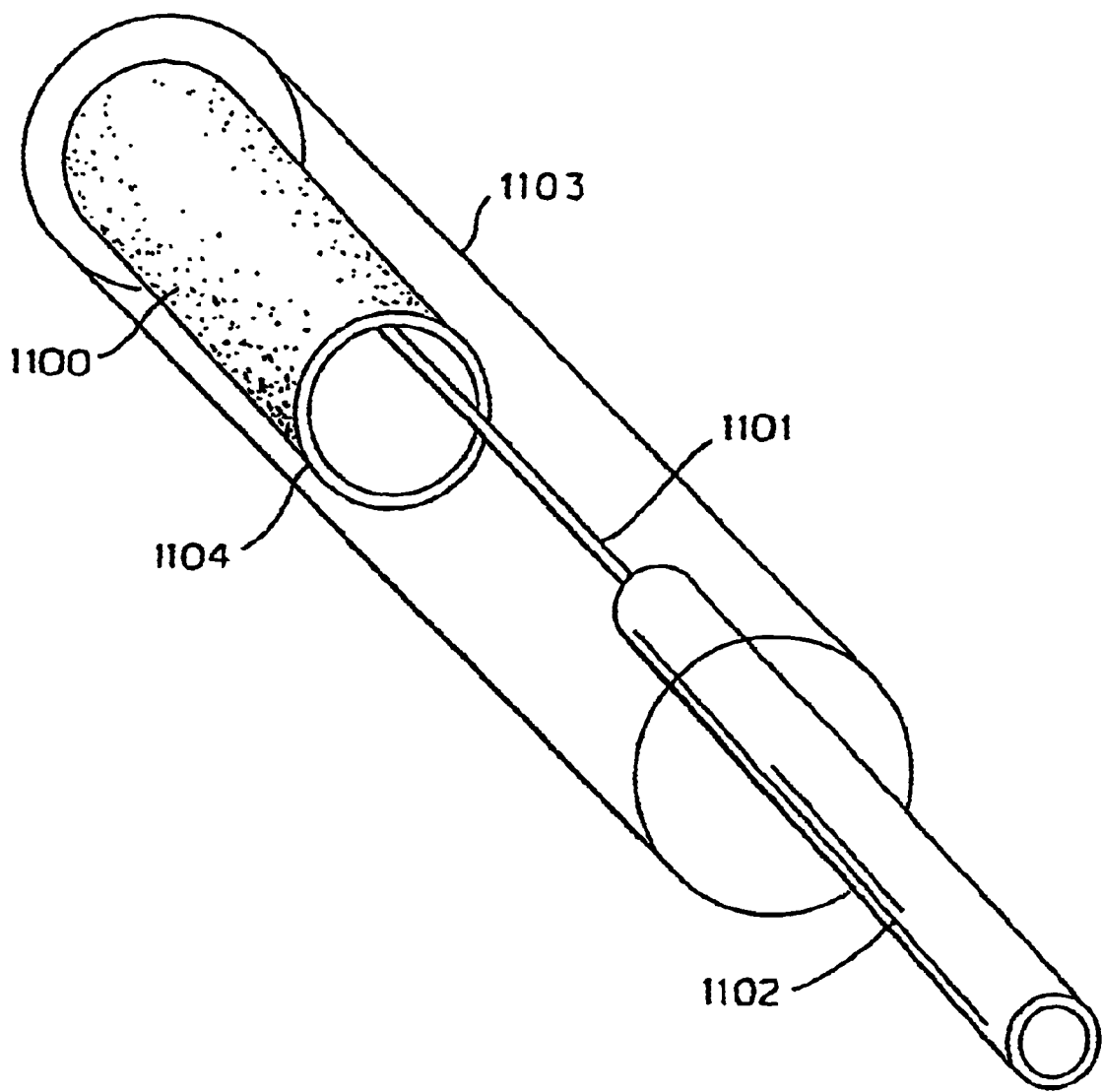
FIG. 11 shows an endovascular thin film device in the form of a distal emboli prevention device depicted as a fenestrated endoluminal conformal closed sleeve in the deployed state.

FIG. 11 shows an endovascular thin film emboli prevention device 1100 in the form of a fenestrated endoluminal conformal closed sleeve in the deployed state. The device is mounted on a nondetachable microguidewire 1101. The device is introduced into the vascular lumen distal to the operative site via a microcatheter 1102. Upon extrusion from the microcatheter, a proximal collapsible ring 1104 unfolds and is sized according to the caliber of the vessel. A shape memory fenestrated thin film closed sleeve 1100 is attached to the proximal ring. The size of the fenestrations is on the order of microns (i.e., 0.1–500 microns) in order to trap small particulate emboli and prevent distal embolization. At the end of the operative procedure, such as angioplasty, when distal protection is no longer required, the microcatheter is brought up to the point of the proximal collapsible ring, and the ring is cinched closed at the microcatheter orifice. The microcatheter and closed sleeve assembly are then removed as one unit by withdrawal into the guiding catheter. The entire assembly, including trapped emboli, can then be safely removed from the patient.

Deployment Methods

An example of deployment methods which can be used in the present invention includes Ampltz "Goose Neck" snares and microsnares. These devices are made of nitinol, which has elastic properties making it possible to manipulate articles within the cardiovascular system.

An example of a catheter and detachable wire and tip for treating the vascular system is described in Guglielmi et al, U.S. Pat. No. 5,354,295, the entire contents of which are hereby incorporated by reference. In this case the wires are stainless steel insulated with Teflon®. The wire is approximately 0.010–0.020 inch (0.254–0.508 mm) in diameter. In one embodiment the guidewire is tapered at its distal end to form a conical section which joins a section of reduced diameter which extends longitudinally along a length of wire. This section of reduced diameter then narrows gradually down to a thin threadlike portion beginning at a first bonding location and ending at a second bonding location.

In the present invention, energy for polymerizing the precursor(s) is provided through the catheter, preferably through an optical fiber assembly for emitting radiation. The optical fiber is embedded within the biocompatible sleeve which is configured to direct energy such that the precursors are polymerized. Preferably, a uniform pattern of energy is produced. The optical fiber may be configured to direct energy outwardly in a generally uniform pattern so as to completely polymerize the precursor(s) to form an endoluminal conformal sleeve or tunnel.

Another advantage of the present invention is that, because there is a relatively limited range of blood vessel calibers, one can use a selection of off-the-shelf conformal sleeve precursors for substantially all patients. Thus, there is no need to individually construct a conformal sleeve precursor for each patient.

Other Applications

While the endovascular thin film devices of the present invention are particularly well suited to treating intracranial aneurysms, the devices of the present invention may be used for treating aneurysms in the extracranial circulation, as well as endovascular repair of arterio-venous fistulas. Additionally, the devices may be used for luminal reconstruction of extracranial vascular segments which are compromised by an encroaching tumor or infection. The devices can also be used to prevent intimal hyperplasia and restenosis following angioplasty. Further, the devices may be adapted for segmental luminal reconstruction and support of a variety of hollow organ systems within the body, including the trachea, esophagus, intestines, bile duct, and the like.

Where appropriate, bioactive agents can be incorporated in the devices. In this case, the precursor material that makes up the device is mixed with a bioactive ingredient and a biodegradable monomer which is also polymerized in situ to form the repair device. As the biodegradable polymer degrades, it releases the bioactive ingredient at the site of the device.

Preferred polymers to mix with the precursors to form an endovascular thin film device which releases active ingredients are polyesters in the polylactide/polyglycolide family. These polymers have received a great deal of attention in the drug delivery and tissue regeneration areas for a number of reasons. They have been in use for over twenty years in surgical sutures, are Food and Drug Administration approved, and have a long and favorable clinical record. A wide range of physical properties and degradation times can be achieved by varying the monomer ratios in lactide/glycolide copolymers: poly-L-lactic acid (PLLA) and polyglycolic acid (PGA) exhibit a high degree of crystallinity and degrade relatively slowly, while copolymers of PLLA and PGA, PLGAs are amorphous and are rapidly degraded. There are essentially no limitations on the bioactive agents that can be incorporated in the repair devices, although those materials which can be processed into particles using spray drying, atomization, grinding or other standard methods, or those materials which can be formed into emulsions, microparticles, liposomes or other small particles, and which remain stable chemically and retain biological activity in a polymeric matrix, are preferred. Bioactive agents also include compounds having principally a structural role, for example, hydroxyapatite crystals in a matrix for bone regeneration. The particles may have a size of greater than or less than the particle size of the polymer particles used to make the repair device.

Examples of such bioactive materials generally include proteins and peptides, nucleic acids, polysaccharides, lipids, and non-protein organic and inorganic compounds, referred to herein as "bioactive agents" unless specifically stated otherwise. These materials have biological effects including, but not limited to, anti-inflammatories, antimicrobials, anti-cancer, antivirals, hormones, antioxidants, channel blockers, and vaccines. It is also possible to incorporate materials not exerting a biological effect, such as air, radiopaque materials, such as barium, or other imaging agents.

The bioactive agents can be incorporated in the devices by adding both the bioactive agent and the biodegradable monomer to the precursor prior to polymerizing the precursor in situ.

The foregoing description of the specific embodiments will so fully reveal the general nature of the invention that others can, by applying current knowledge, readily modify nd/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

All of the references cited herein are hereby incorporated by reference in their entirety.

What is claimed is:

1. A thin-film device consisting of an expanse of spattered thin film NiTi shape memory alloy, for delivery to an endoluminal target body site via a catheter or guide-wire guide assembly, comprising an expanse of sputtered thin-film Ni-Ti shape-memory alloy having a film thickness between about 0.5 to 150 microns, and characterized by
  (i) a martensitic state,
  (ii) an austenitic state in which the expanse assumes a preformed, expanded shape about the member, with such in its deployed condition, and
  (iii) a thin-film transition temperature at which the expanse undergoes a transition from its martensitic state to its austenitic: state, wherein deployment of the device at a site having a temperature above the transition temperature is effective to place the expanse in its preformed shape.

2. The device of claim 1, wherein said expanse has a thickness of between 2 and 50 microns.

3. The device of claim 1, for use at an endoluminal site that is accessible by means of a catheter having an inner lumen, wherein the device is dimensioned to be advanced through the catheter lumen, with the device in its martensite state.

4. The device of claim 1, wherein said expanse is fenestrated.

5. The device of claim 1, for use as an endoluminal stent, wherein said expanse, in its preformed, austenitic shape, forms an open-sided, closed or overlapping-edge tubular sleeve dimensioned to contact the wall segment of the vessel target site, to hold the device in place when deployed at the site.

6. The device of claim 5, which contains a partial, non-circumferential fenestration.

7. The device of claim 1, for use as a bifurcated-vessel stent, wherein said expanse, in its preformed, austenitic shape, forms a bifurcated tubular sleeve having a single proximal and first and second distal ends and the device is dimensioned to contact the wall segments of the bifurcated-vessel target site, to hold the device in place when deployed at the site.

8. The device of claim 1, for use in retrieving macroscopic objects, such as blood clots, from a blood vessel, wherein said expanse, in its preformed, austenitic shape, forms a sock having an open proximal end, and the device further includes a remote-access wire attached to the expanse for moving the device in a target vessel.

9. The device of claim 8, wherein at least a portion of the expanse is fenestrated to allow blood flow through the expanse.

10. The device of claim 1, for use as an intra-aneurysmal occlusion device, wherein said expanse, in its preformed, austenitic shape, forms a conical or hemispherical funnel or a sphere having a distal opening, and the distal opening is larger than the aneurysmal opening through which the device is deployed by a catheter.

11. The device of claim 10, which further includes a proximal valved opening through which vaso-occlusive material can be introduced into the aneurysm, when the device is deployed therein.

12. The device of claim 10, wherein said expanse includes a plurality of overlapping segments which, in their preformed, austenitic state, form a conical or hemispherical funnel having a distal opening, and the distal opening is larger than the aneurysmal opening through which the device is deployed by a catheter.

13. The device of claim 12, which further includes a proximal valved opening through which vaso-occlusive material can be introduced into the aneurysm, when the device is deployed therein.

14. The device of claim 10, wherein said expanse forms a space-filling expanse.

* * * * *